(12) United States Patent
Daniels

(10) Patent No.: US 12,676,232 B2
(45) Date of Patent: Jul. 7, 2026

(54) MASK-BASED DIAGNOSTIC UTILIZING AI ALGORITHMS FOR IMPROVED PATIENT OUTCOMES

(71) Applicant: John J. Daniels, Madison, CT (US)

(72) Inventor: John J. Daniels, Madison, CT (US)

( * ) Notice: Subject to any disclaimer, the term of this patent is extended or adjusted under 35 U.S.C. 154(b) by 0 days.

(21) Appl. No.: 18/357,870

(22) Filed: Jul. 24, 2023

(65) Prior Publication Data

US 2024/0347191 A1 Oct. 17, 2024

Related U.S. Application Data

(63) Continuation of application No. 18/301,967, filed on Apr. 17, 2023.

(51) Int. Cl.
*A61B 5/097* (2006.01)
*A61B 5/00* (2006.01)
(Continued)

(52) U.S. Cl.
CPC ........... *G16H 40/67* (2018.01); *A61B 5/0006* (2013.01); *A61B 5/02444* (2013.01); *A61B 5/097* (2013.01)

(58) Field of Classification Search
CPC ........ G16H 40/67; G16H 50/20; G16H 50/30; G16H 50/80; G16H 50/70;
(Continued)

(56) References Cited

U.S. PATENT DOCUMENTS 4,158,196 A 6/1979 Crawford, Jr.
5,637,176 A 6/1997 Gilleo et al.
(Continued)

FOREIGN PATENT DOCUMENTS

CN 104225791 6/2013
CN 104220128 7/2016
(Continued)

OTHER PUBLICATIONS

A Deep-Learning-Assisted On-Mask Sensor Network for Adaptive Respiratory Monitoring, Advanced Materials by Yunsheng Fang, Jing Xu, Xiao Xiao, Youngjiu Zou, Xun Zhao, Yihao Zhou, Jun Chen, vol. 34, Issue 24, Mar. 22, 2022 (Year: 2022).*
(Continued)

*Primary Examiner* — Alaaeldin M. Elshaer
*Assistant Examiner* — Teresa S Williams
(74) *Attorney, Agent, or Firm* — John J. Daniels; David J. Powsner

(57) ABSTRACT

A mask-based diagnostic (MBD) system for remote patient monitoring that collects chemical biomarker data and non-chemical biometric data from patients in a non-invasive manner. The MBD can be used to monitor various medical conditions, including cardiovascular disease, lung cancer, diabetes, and respiratory diseases. The system consists of a mask having an exhaled breath condensate (EBC) collector that tests for chemical biomarkers in EBC. Non-chemical biometric data, such as temperature, heart rate, and blood oxygen levels can also be obtained using a wearable electronic device. The collected data is transmitted wirelessly to a remote server for aggregation, analysis, and interpretation using artificial intelligence (AI) algorithms. The AI algorithms detect patterns and trends in the patient data, which can be used for drug discovery, to identify health issues, adjust treatment plans, etc. The MBD can improve patient outcomes by providing real-time monitoring, early detection of health issues, and personalized treatment options.

32 Claims, 12 Drawing Sheets

(51) Int. Cl.
   *A61B 5/024* (2006.01)
   *G16H 40/67* (2018.01)
(58) Field of Classification Search
   CPC ........ A61B 2017/00044; A61B 5/0006; A61B
                   5/02444; A61B 5/01; A61B 5/7267
   USPC .......................................................... 705/2
   See application file for complete search history.

(56) References Cited

U.S. PATENT DOCUMENTS

| | | | |
|---|---|---|---|
| 6,316,274 | B1 | 11/2001 | Herron et al. |
| 6,411,276 | B1 | 6/2002 | Braun et al. |
| 6,464,171 | B2 | 10/2002 | Ruffin |
| 6,609,018 | B2 | 8/2003 | Cory et al. |
| 6,892,098 | B2 | 5/2005 | Ayal et al. |
| 6,908,572 | B1 | 6/2005 | Derbyshire et al. |
| 6,930,590 | B2 | 8/2005 | Ling et al. |
| 6,965,842 | B2 | 11/2005 | Rekimoto |
| 7,013,179 | B2 | 3/2006 | Carter et al. |
| 7,052,854 | B2 | 5/2006 | Melker |
| 7,228,178 | B2 | 6/2007 | Carroll et al. |
| 7,261,812 | B1 | 8/2007 | Karp et al. |
| 7,539,724 | B1 | 5/2009 | Callaghan |
| 7,779,840 | B2 | 8/2010 | Acker et al. |
| 8,002,712 | B2 | 8/2011 | Meka |
| 8,098,046 | B2 | 1/2012 | Poisner |
| 8,130,093 | B2 | 3/2012 | Mazar et al. |
| 8,280,503 | B2 | 10/2012 | Linderman |
| 8,378,964 | B2 | 2/2013 | Ullrich et al. |
| 8,394,030 | B2 | 3/2013 | Varga et al. |
| 8,552,847 | B1 | 10/2013 | Hill |
| 8,560,082 | B2 | 10/2013 | Wei |
| 8,617,228 | B2 | 12/2013 | Wittenberger et al. |
| 8,620,434 | B2 | 12/2013 | Bodlaender |
| 9,022,029 | B2 | 5/2015 | Care |
| 9,169,521 | B1 | 10/2015 | Rajagopal et al. |
| 9,357,946 | B2 | 6/2016 | Johnson |
| 9,390,630 | B2 | 7/2016 | Daniels |
| 9,435,788 | B2 | 9/2016 | Killard et al. |
| 9,746,985 | B1 * | 8/2017 | Humayun ............. G06F 16/904 |
| 9,874,563 | B2 | 1/2018 | Zurakowski |
| 9,968,281 | B2 | 5/2018 | Exhalation |
| 10,048,213 | B2 | 8/2018 | Wilds |
| 10,238,079 | B1 | 3/2019 | Eby |
| 10,274,487 | B2 | 4/2019 | Ludwig |
| 10,381,826 | B2 | 8/2019 | Gao |
| 10,393,753 | B2 | 8/2019 | Milton |
| 10,437,335 | B2 | 10/2019 | Daniels |
| 10,463,275 | B2 | 11/2019 | King-Smith |
| 10,481,688 | B1 | 11/2019 | Wang |
| 10,589,277 | B2 | 3/2020 | Invoy |
| 10,617,363 | B2 | 4/2020 | Diebold et al. |
| 10,670,580 | B2 | 6/2020 | Javanmard et al. |
| 10,687,764 | B2 | 6/2020 | Bastide et al. |
| 10,753,949 | B2 | 8/2020 | Grafman et al. |
| 10,859,473 | B2 | 12/2020 | Wu et al. |
| 12,251,188 | B2 * | 3/2025 | Hodge ................... G16H 20/13 |
| 2001/0023076 | A1 | 9/2001 | Guan |
| 2002/0125135 | A1 | 9/2002 | Derand |
| 2002/0130311 | A1 | 9/2002 | Lieber et al. |
| 2003/0068053 | A1 | 4/2003 | Chu |
| 2003/0149457 | A1 | 8/2003 | Tcheng et al. |
| 2003/0170602 | A1 | 9/2003 | Hagita et al. |
| 2004/0019301 | A1 | 1/2004 | Wong et al. |
| 2004/0023514 | A1 | 2/2004 | Moriya et al. |
| 2004/0057176 | A1 | 3/2004 | Dhawan |
| 2004/0112964 | A1 | 6/2004 | Empedocles et al. |
| 2004/0174431 | A1 | 9/2004 | Stienstra |
| 2004/0244564 | A1 | 12/2004 | McGregor |
| 2005/0101841 | A9 | 5/2005 | Kaylor |
| 2006/0137511 | A1 | 6/2006 | McGregor |
| 2007/0000374 | A1 | 1/2007 | Clark et al. |
| 2007/0031283 | A1 | 2/2007 | Davis et al. |
| 2007/0068810 | A1 | 3/2007 | Tsukashima et al. |
| 2007/0110613 | A1 | 5/2007 | Pachl et al. |
| 2007/0250119 | A1 | 10/2007 | Tyler et al. |
| 2007/0282228 | A1 | 12/2007 | Einav et al. |
| 2008/0045825 | A1 | 2/2008 | Melker et al. |
| 2008/0103639 | A1 | 5/2008 | Troy et al. |
| 2008/0185295 | A1 | 8/2008 | Briman et al. |
| 2008/0188306 | A1 | 8/2008 | Tetterington |
| 2008/0214947 | A1 | 9/2008 | Hunt et al. |
| 2008/0300798 | A1 | 12/2008 | McDevitt et al. |
| 2009/0053683 | A1 | 2/2009 | Brown et al. |
| 2009/0231276 | A1 | 9/2009 | Ullrich et al. |
| 2009/0255535 | A1 | 10/2009 | Kanzer |
| 2009/0326406 | A1 | 12/2009 | Tan et al. |
| 2010/0087749 | A1 | 4/2010 | Tovey |
| 2010/0106044 | A1 | 4/2010 | Linderman |
| 2010/0169119 | A1 | 7/2010 | Hussain |
| 2011/0048213 | A1 | 3/2011 | Choi et al. |
| 2011/0094306 | A1 | 4/2011 | Bratkovski |
| 2011/0183304 | A1 | 7/2011 | Wallace |
| 2011/0238079 | A1 | 9/2011 | Hannaford et al. |
| 2012/0035513 | A1 | 2/2012 | Afshar |
| 2012/0094263 | A1 | 4/2012 | Seitz |
| 2012/0167747 | A1 | 7/2012 | Luchinskiy |
| 2012/0216666 | A1 | 8/2012 | Fresolone |
| 2012/0260789 | A1 | 10/2012 | Ur et al. |
| 2013/0029791 | A1 | 1/2013 | Rose et al. |
| 2013/0118339 | A1 | 5/2013 | Lee et al. |
| 2013/0207890 | A1 | 8/2013 | Young |
| 2013/0209980 | A1 | 8/2013 | Kuchenbecker |
| 2013/0310122 | A1 | 11/2013 | Piccionielli |
| 2014/0038139 | A1 | 2/2014 | AlDossary |
| 2014/0180361 | A1 | 6/2014 | Burdick et al. |
| 2014/0186810 | A1 | 7/2014 | Falash et al. |
| 2014/0208204 | A1 | 7/2014 | Lacroix et al. |
| 2014/0240103 | A1 | 8/2014 | Lake et al. |
| 2014/0248594 | A1 | 9/2014 | Navas |
| 2014/0282105 | A1 | 9/2014 | Nordstrom |
| 2014/0364758 | A1 | 12/2014 | Schindhelm et al. |
| 2015/0024381 | A1 | 1/2015 | Zurakowski |
| 2015/0050623 | A1 | 2/2015 | Falash et al. |
| 2015/0140528 | A1 | 5/2015 | Sikstrom et al. |
| 2015/0140529 | A1 | 5/2015 | Tinjust |
| 2015/0221230 | A1 | 8/2015 | Karadjian et al. |
| 2015/0269863 | A1 | 9/2015 | Shrewsbury |
| 2015/0279238 | A1 | 10/2015 | Forte et al. |
| 2015/0294585 | A1 | 10/2015 | Kullok et al. |
| 2015/0294597 | A1 | 10/2015 | Rizzo |
| 2015/0302763 | A1 | 10/2015 | Gleim et al. |
| 2015/0314195 | A1 | 11/2015 | Bekri |
| 2015/0317910 | A1 | 11/2015 | Daniels |
| 2015/0323993 | A1 | 11/2015 | Levesque et al. |
| 2016/0030751 | A1 | 2/2016 | Ghosh et al. |
| 2016/0150992 | A1 | 6/2016 | Lee |
| 2016/0224750 | A1 | 8/2016 | Kethman et al. |
| 2017/0056644 | A1 | 3/2017 | Chahine et al. |
| 2017/0072369 | A1 | 3/2017 | Mitra et al. |
| 2017/0273864 | A1 | 9/2017 | Kaufman et al. |
| 2017/0356899 | A1 | 12/2017 | Guder et al. |
| 2017/0358235 | A1 | 12/2017 | Daniels |
| 2017/0370030 | A1 | 12/2017 | Podhajny et al. |
| 2018/0068083 | A1 | 3/2018 | Cohen et al. |
| 2018/0108440 | A1 | 4/2018 | Stevens |
| 2018/0144092 | A1 | 5/2018 | Flitsch et al. |
| 2018/0242884 | A1 | 8/2018 | Kulkarni et al. |
| 2018/0303383 | A1 | 10/2018 | Connor |
| 2018/0322941 | A1 | 11/2018 | Krishnan |
| 2019/0056788 | A1 | 2/2019 | Piper et al. |
| 2019/0076647 | A1 | 3/2019 | Tamaki et al. |
| 2019/0131016 | A1 | 5/2019 | Cohen et al. |
| 2019/0136423 | A1 | 5/2019 | Podhajny et al. |
| 2019/0142350 | A1 | 5/2019 | Bastide et al. |
| 2019/0201619 | A1 | 7/2019 | Gibson et al. |
| 2019/0317115 | A1 | 10/2019 | Maclean |
| 2020/0041485 | A1 | 2/2020 | Fuinch-Nielsen |
| 2020/0155069 | A1 | 5/2020 | Bogdanovich et al. |
| 2020/0281504 | A1 | 9/2020 | Invoy |
| 2020/0384470 | A1 | 12/2020 | Huff et al. |
| 2021/0198872 | A1 | 7/2021 | Colman et al. |
| 2021/0321903 | A1 | 10/2021 | Daniels |

(56)                References Cited

U.S. PATENT DOCUMENTS

| 2021/0325279 | A1 |  | 10/2021 | Daniels |  |
|---|---|---|---|---|---|
| 2021/0325381 | A1 |  | 10/2021 | Daniels |  |
| 2021/0325382 | A1 |  | 10/2021 | Daniels |  |
| 2021/0375459 | A1 | * | 12/2021 | Longmire | G16H 10/60 |
| 2021/0382045 | A1 |  | 12/2021 | Aran et al. |  |
| 2022/0034854 | A1 |  | 2/2022 | Chen |  |
| 2022/0061823 | A1 | * | 3/2022 | Berger | G01N 33/497 |
| 2022/0139556 | A1 | * | 5/2022 | Unnikrishnan | G16H 50/20 |
|  |  |  |  |  | 705/2 |
| 2022/0157456 | A1 | * | 5/2022 | Luckow | G16H 80/00 |
| 2022/0322963 | A1 |  | 10/2022 | Chen |  |
| 2023/0040102 | A1 | * | 2/2023 | Bonistalli | A61B 5/0205 |
| 2023/0088974 | A1 | * | 3/2023 | Kim | G16H 50/20 |
|  |  |  |  |  | 705/2 |
| 2023/0200678 | A1 |  | 6/2023 | Daniels |  |
| 2023/0333038 | A1 |  | 10/2023 | Daniels |  |
| 2023/0346299 | A1 | * | 11/2023 | Waterhouse | A61B 5/0022 |

FOREIGN PATENT DOCUMENTS

| CN |  | 106644606 |  | 5/2017 |  |  |
|---|---|---|---|---|---|---|
| CN |  | 108883335 |  | 11/2018 |  |  |
| CN |  | 110381826 |  | 10/2019 |  |  |
| CN |  | 111387950 |  | 7/2020 |  |  |
| EP |  | 2801389 |  | 11/2014 |  |  |
| EP |  | 3544495 |  | 10/2019 |  |  |
| JP |  | 2020516327 | A | 6/2020 |  |  |
| WO | WO | 1997004310 |  | 6/1997 |  |  |
| WO | WO | 2010002993 |  | 7/2010 |  |  |
| WO | WO | 2013071307 |  | 5/2013 |  |  |
| WO | WO | 2014038049 |  | 3/2014 |  |  |
| WO | WO-2014040175 | A1 | * | 3/2014 | A61B 5/0006 |
| WO | WO | 2014113813 |  | 7/2014 |  |  |
| WO | WO | 2015124580 |  | 8/2015 |  |  |
| WO | WO | 2015166444 |  | 11/2015 |  |  |
| WO | WO | 2016168117 |  | 10/2016 |  |  |
| WO | WO | 2017048881 |  | 3/2017 |  |  |
| WO | WO | 2018098046 |  | 5/2018 |  |  |
| WO | WO | 2019046712 |  | 3/2019 |  |  |
| WO | WO | 2019178247 |  | 9/2019 |  |  |
| WO | WO | 2020176607 |  | 9/2020 |  |  |
| WO | WO | 2020234338 |  | 11/2020 |  |  |
| WO | WO | 2020257356 |  | 12/2020 |  |  |
| WO | WO | 2021041571 |  | 3/2021 |  |  |
| WO | WO | 2021216386 |  | 10/2021 |  |  |
| WO | WO | 2023023481 |  | 2/2023 |  |  |
| WO | WO | 2023023678 |  | 2/2023 |  |  |
| WO | WO | 2023205574 |  | 10/2023 |  |  |

OTHER PUBLICATIONS

U.S. Appl. No. 16/876,054, Using Exhaled Breath Condensate for Testing for a Biomarker of Covid-19.
U.S. Appl. No. 16/882,447, Using Exhaled Breath Condensate, Aerosols and Gases for Detecting Biomarkers.
U.S. Appl. No. 17/065,488, Mask-Based Testing System for Detecting Biomarkers in Exhaled Breath Condensate, Aerosols and Gases.
U.S. Appl. No. 17/189,711, Mask-Based Diagnostic System Using Exhaled Breath Condensate.
U.S. Appl. No. 17/864,343, Mask-Based Diagnostic Device and Wafer-Level Functionalization of a Packaged Semiconductor Biosensor.
U.S. Appl. No. 18/046,911, Mask-Based Diagnostic System Using Exhaled Breath Condensate.
U.S. Appl. No. 18/113,777, Mask-Based Diagnostic Device With Accessibility Features.
U.S. Appl. No. 18/301,967, Mask-Based Diagnostic Utilizing Ai Algorithms for Improved Patient Outcomes.
U.S. Appl. No. 18/357,870, Mask-Based Diagnostic Utilizing Ai Algorithms for Improved Patient Outcomes.
U.S. Appl. No. 63/012,247, Low Cost, Scalable, Accurate, and Easy-to-Use Testing System for Covid-19.

U.S. Appl. No. 63/019,378, Using Exhaled Breath Condensate for Testing for a Biomarker of Covid-19.
U.S. Appl. No. 63/026,052, Using Exhaled Breath Condensate forTesting for a Biomarker of Covid-19.
U.S. Appl. No. 63/233,473, Diagnostic Platform for Testing Exhaled Breath Condensate.
U.S. Appl. No. 62/945,995, Diagnostic Platform for Testing Exhaled Breath Condensate and Universal Biosensor.
U.S. Appl. No. 63/331,841, Mask-Based Diagnostic Device and Packaged Semiconductor Biosensor.
PCT/US21/24404, Mask-Based Diagnostic System Using Exhaled Breath Condensate.
PCT/US21/27740, Mask-Based Diagnostic System Using Exhaled Breath Condensate.
PCT/US21/27854, Mask-Based Diagnostic System Using Exhaled Breath Condensate.
PCT/US22/74961, Diagnostic Platform for Testing Exhaled Breath Condensate.
PCT/US22/76511, Diagnostic Platform for Testing Exhaled Breath Condensate and Universal Biosensor.
PCT/US23/65562, Mask-Based Diagnostic Device and Wafer-Level Functionalization of a Packaged Semiconductor Biosensor.
Nguyen, Wearable materials with embedded synthetic biology sensors for biomolecule detection, Nature Biotechnology, vol. 39, Nov. 2021, 1366-1374.
Maier et al., "Toward Continuous Monitoring of Breath Biochemistry: A Paper-Based Wearable Sensor for Real-Time Hydrogen Peroxide Measurement in Simulated Breath", 2019, ACS Sensors, vol. 4, p. 2945-2951 (Year: 2019).
Bhardwaj et al., "Recent advancements in the measurement of pathogenic airborne viruses", 2021, Journal of Hazardous Materials, vol. 420 (Year: 2021).
Li et al., "Comparing the performance of 3 bioaerosol samplers for influenza virus", 2018, Journal of Aerosol Science, vol. 115 (Year: 2018).
Zhao et al., "Airborne virus sampling—Efficiencies of samplers and their detection limits for infectious bursal disease virus (IBDV)", 2014, Annals of Agricultural and Environmental Medicine, vol. 21 (Year: 2014).
Daniels et al., A mask-based diagnostic platform for point-of-care screening of Covid-19, Biosensors and Bioelectronics. Jul. 8, 2021, vol. 192, pp. 1-8.
Bhardwaj et al., Recent progress in nanomaterial-based sensing of airborne viral and bacterial pathogens. Environment International. Oct. 25, 2020, vol. 146, No. 106183, pp. 1-18.
Hajian et al., Detection of unamplified target genes via CRISPR-Cas9 immobilized on a graphene field-effect transistor. Nature Biomedical Engineering. Jun. 2019, vol. 3, No. 6, pp. 427-437.
Kim et al., Bio-inspired catechol conjugation converts water-insoluble chitosan into a highly water-soluble, adhesive chitosan derivative for hydrogels and LbL assembly. Biomaterials Science. May 2, 2013, vol. 1, pp. 783-790.
Kim et al., Nanowire-integrated microfluidic devices for facile and reagent-free mechanical cell lysis. Lab on a Chip. May 15, 2012, vol. 12, pp. 2914-2921.
Li et al., Rapid and unamplified identification of COVID-19 with morpholino-modified graphene field-effect transistor nanosensor. Biosensors and Bioelectronics. Mar. 30, 2021, vol. 183, pp. 1-9.
Sadir, S., Interfacial Wicking Flow Through Hierarchical Structure of Natural Cellulose Fibers for Biomedical Microfluidic Devices. Dissertation. Universiti Teknologi Malaysia. Nov. 2015 [online]. [Retrieved on Mar. 7, 2023]. Retrieved from the internet: <URL: http://eprints.utm.my/Id/eprint/78509/1/SahbaSadirMFKM2015>.
Xie et al., "Nanofiltration" Enabled by Super-Absorbent Polymer Beads for Concentrating Microorganisms in Water Samples. Nature. Feb. 15, 2016, vol. 6, No. 20516, pp. 1-8.
Sorribas et al., Photolithographic generation of protein micropatterns for neuron culture applications. Biomaterials. Feb. 2002, vol. 23, No. 3, pp. 893-900.
International Search Report and Written Opinion mailed Oct. 6, 2021 for related PCT application Serial No. PCT/US21/27854, ISA/USA.

(56)        References Cited

OTHER PUBLICATIONS

International Search Report and Written Opinion mailed Feb. 17, 2023 for related PCT application Serial No. PCT/US22/074961, ISA/USA.

International Search Report and Written Opinion mailed Apr. 24, 2023 for related PCT application Serial No. PCT/US22/076511, ISA/USA.

International Search Report and Written Opinion mailed Sep. 28, 2023 for related PCT application Serial No. PCT/US23/065562, ISA/USA.

U.S. Appl. No. 14/269,133, Accelerated Learning, Entertainment and Cognitive Therapy Using Augmented Reality Comprising Combined Haptic, Auditory, and Visual Stimulation, filed May 3, 2014.

U.S. Appl. No. 15/177,373, Accelerated Learning, Entertainment and Cognitive Therapy Using Augmented Reality Comprising Combined Haptic, Auditory, and Visual Stimulation, filed Jun. 9, 2016.

U.S. Appl. No. 15/562,752, Wearable Electronic, Multi-Sensory, Human/Machine, Human/Human Interfaces, filed Sep. 28, 2017.

U.S. Appl. No. 16/464,171, Haptic Human Machine Interface and Wearable Electronics Methods and Apparatus, filed May 24, 2019.

U.S. Appl. No. 16/737,055, Fabric, Connections and Functional Structures for Wearable Electronic Garments and Applications for the Same, filed Jan. 8, 2020.

U.S. Appl. No. 16/910,626, Wearable Electronic Haptic Feedback System for VR/AR and Gaming, Jun. 24, 2020.

U.S. Appl. No. 17/201,091, Methods and Apparatus for a Wearable Electronic Digital Therapeutic Device, filed Mar. 15, 2021.

U.S. Appl. No. 17/481,240, Accelerated Learning, Entertainment and Cognitive Therapy Using Augmented Reality Comprising Combined Haptic, Auditory, and Visual Stimulation, filed Sep. 21, 2021.

U.S. Appl. No. 63/327,921, Wearable Electronic for Monitoring a Change in a Physical Condition of a Patient, Apr. 6, 2022.

PCT/US19/45429, Methods and Apparatus for a Wearable Electronic Digital Therapeutic Device.

PCT/US23/65316, Wearable Electronic for Digital Healthcare.

* cited by examiner

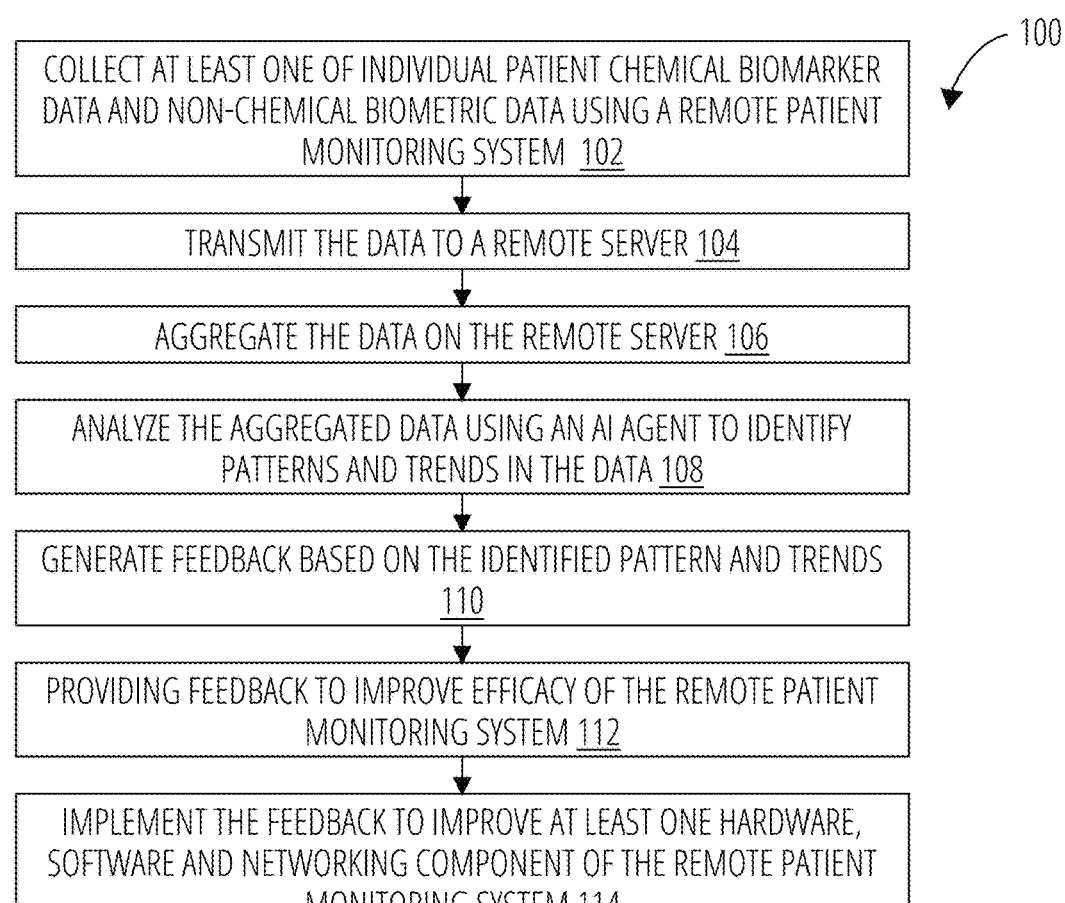

```
                                                                        ┌─ 100
COLLECT AT LEAST ONE OF INDIVIDUAL PATIENT CHEMICAL BIOMARKER
DATA AND NON-CHEMICAL BIOMETRIC DATA USING A REMOTE PATIENT
              MONITORING SYSTEM 102
                        │
                        ▼
        TRANSMIT THE DATA TO A REMOTE SERVER 104
                        │
                        ▼
        AGGREGATE THE DATA ON THE REMOTE SERVER 106
                        │
                        ▼
  ANALYZE THE AGGREGATED DATA USING AN AI AGENT TO IDENTIFY
          PATTERNS AND TRENDS IN THE DATA 108
                        │
                        ▼
  GENERATE FEEDBACK BASED ON THE IDENTIFIED PATTERN AND TRENDS
                       110
                        │
                        ▼
 PROVIDING FEEDBACK TO IMPROVE EFFICACY OF THE REMOTE PATIENT
              MONITORING SYSTEM 112
                        │
                        ▼
 IMPLEMENT THE FEEDBACK TO IMPROVE AT LEAST ONE HARDWARE,
 SOFTWARE AND NETWORKING COMPONENT OF THE REMOTE PATIENT
              MONITORING SYSTEM 114
```

Figure 2:
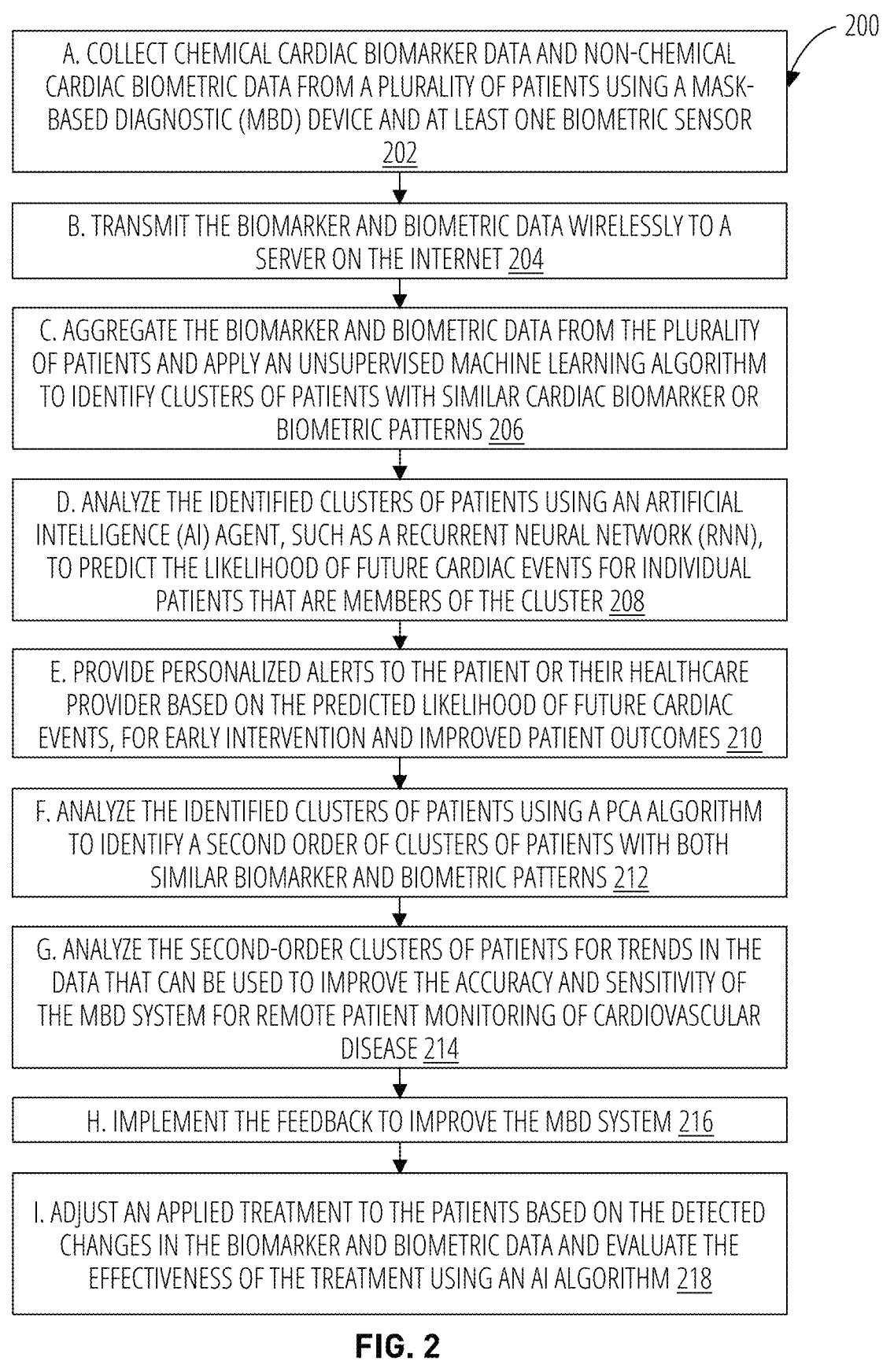

A. COLLECT CHEMICAL CARDIAC BIOMARKER DATA AND NON-CHEMICAL CARDIAC BIOMETRIC DATA FROM A PLURALITY OF PATIENTS USING A MASK-BASED DIAGNOSTIC (MBD) DEVICE AND AT LEAST ONE BIOMETRIC SENSOR 202

↓

B. TRANSMIT THE BIOMARKER AND BIOMETRIC DATA WIRELESSLY TO A SERVER ON THE INTERNET 204

↓

C. AGGREGATE THE BIOMARKER AND BIOMETRIC DATA FROM THE PLURALITY OF PATIENTS AND APPLY AN UNSUPERVISED MACHINE LEARNING ALGORITHM TO IDENTIFY CLUSTERS OF PATIENTS WITH SIMILAR CARDIAC BIOMARKER OR BIOMETRIC PATTERNS 206

↓

D. ANALYZE THE IDENTIFIED CLUSTERS OF PATIENTS USING AN ARTIFICIAL INTELLIGENCE (AI) AGENT, SUCH AS A RECURRENT NEURAL NETWORK (RNN), TO PREDICT THE LIKELIHOOD OF FUTURE CARDIAC EVENTS FOR INDIVIDUAL PATIENTS THAT ARE MEMBERS OF THE CLUSTER 208

↓

E. PROVIDE PERSONALIZED ALERTS TO THE PATIENT OR THEIR HEALTHCARE PROVIDER BASED ON THE PREDICTED LIKELIHOOD OF FUTURE CARDIAC EVENTS, FOR EARLY INTERVENTION AND IMPROVED PATIENT OUTCOMES 210

↓

F. ANALYZE THE IDENTIFIED CLUSTERS OF PATIENTS USING A PCA ALGORITHM TO IDENTIFY A SECOND ORDER OF CLUSTERS OF PATIENTS WITH BOTH SIMILAR BIOMARKER AND BIOMETRIC PATTERNS 212

↓

G. ANALYZE THE SECOND-ORDER CLUSTERS OF PATIENTS FOR TRENDS IN THE DATA THAT CAN BE USED TO IMPROVE THE ACCURACY AND SENSITIVITY OF THE MBD SYSTEM FOR REMOTE PATIENT MONITORING OF CARDIOVASCULAR DISEASE 214

↓

H. IMPLEMENT THE FEEDBACK TO IMPROVE THE MBD SYSTEM 216

↓

I. ADJUST AN APPLIED TREATMENT TO THE PATIENTS BASED ON THE DETECTED CHANGES IN THE BIOMARKER AND BIOMETRIC DATA AND EVALUATE THE EFFECTIVENESS OF THE TREATMENT USING AN AI ALGORITHM 218

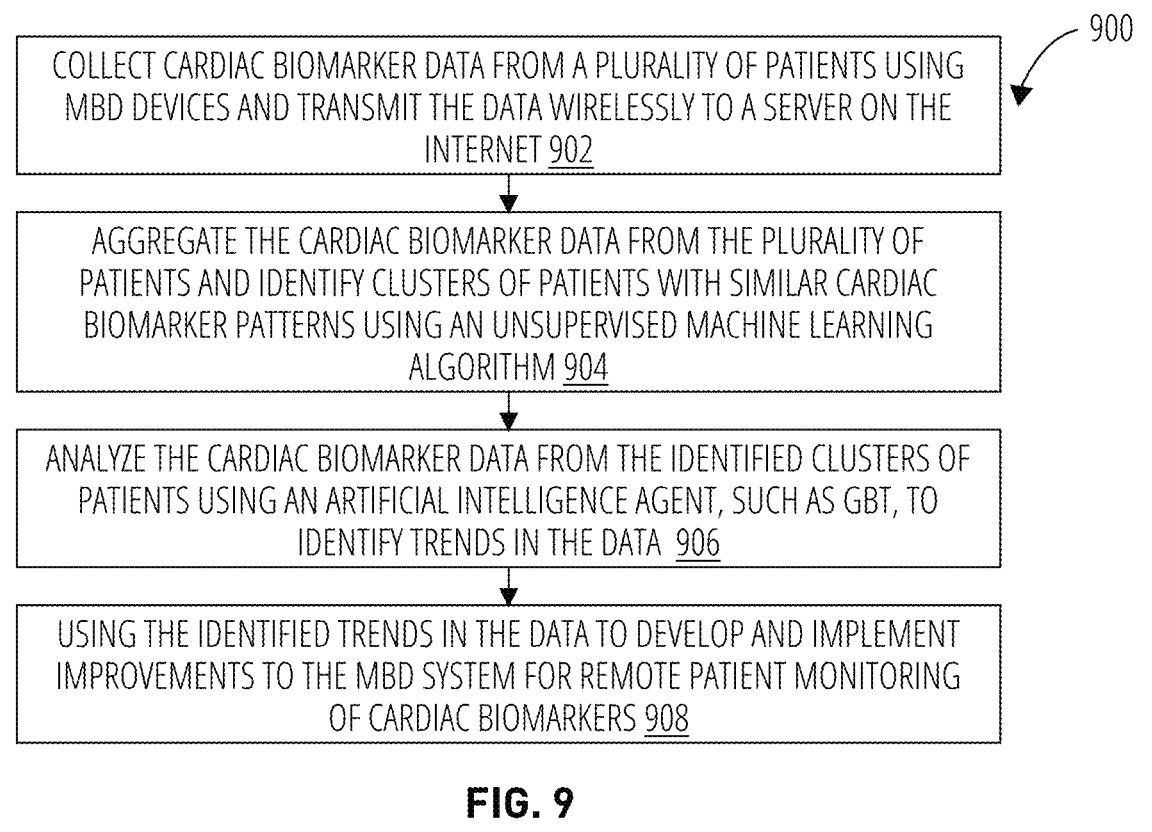

COLLECT CARDIAC BIOMARKER DATA FROM A PLURALITY OF PATIENTS USING MBD DEVICES AND TRANSMIT THE DATA WIRELESSLY TO A SERVER ON THE INTERNET 902

AGGREGATE THE CARDIAC BIOMARKER DATA FROM THE PLURALITY OF PATIENTS AND IDENTIFY CLUSTERS OF PATIENTS WITH SIMILAR CARDIAC BIOMARKER PATTERNS USING AN UNSUPERVISED MACHINE LEARNING ALGORITHM 904

ANALYZE THE CARDIAC BIOMARKER DATA FROM THE IDENTIFIED CLUSTERS OF PATIENTS USING AN ARTIFICIAL INTELLIGENCE AGENT, SUCH AS GBT, TO IDENTIFY TRENDS IN THE DATA  906

USING THE IDENTIFIED TRENDS IN THE DATA TO DEVELOP AND IMPLEMENT IMPROVEMENTS TO THE MBD SYSTEM FOR REMOTE PATIENT MONITORING OF CARDIAC BIOMARKERS 908

FIG. 9

A) COLLECT CARDIAC BIOMARKER DATA FROM A PATIENT USING A MASK-BASED DIAGNOSTIC (MBD) DEVICE AND TRANSMIT THE DATA WIRELESSLY TO A SERVER ON THE INTERNET 1002

B) ANALYZE THE CARDIAC BIOMARKER DATA USING AN ARTIFICIAL INTELLIGENCE (AI) AGENT TO IDENTIFY TRENDS IN THE DATA AND PREDICT THE LIKELIHOOD OF FUTURE CARDIAC EVENTS FOR THE INDIVIDUAL PATIENT 1004

C) PROVIDE PERSONALIZED ALERTS TO THE PATIENT OR THEIR HEALTHCARE PROVIDER BASED ON THE PREDICTED LIKELIHOOD OF FUTURE CARDIAC EVENTS, FOR EARLY INTERVENTION AND IMPROVED PATIENT OUTCOMES 1006

FIG. 10

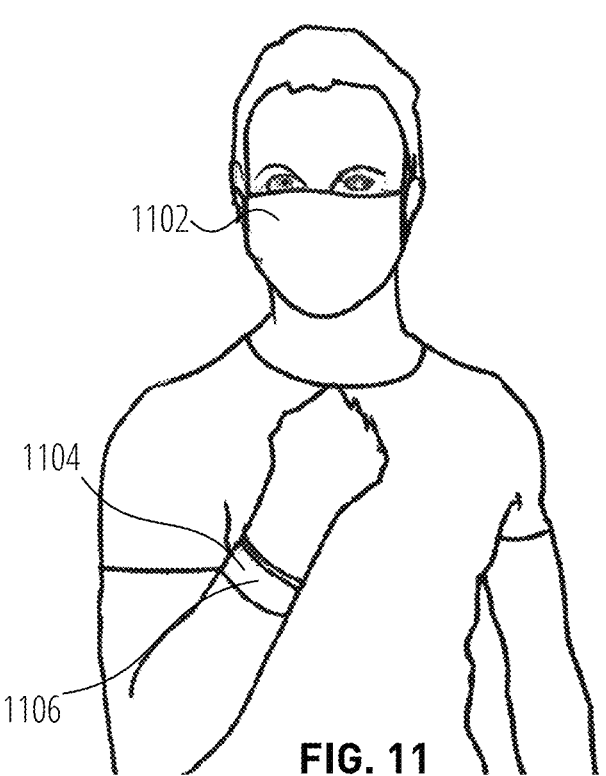

FIG. 11

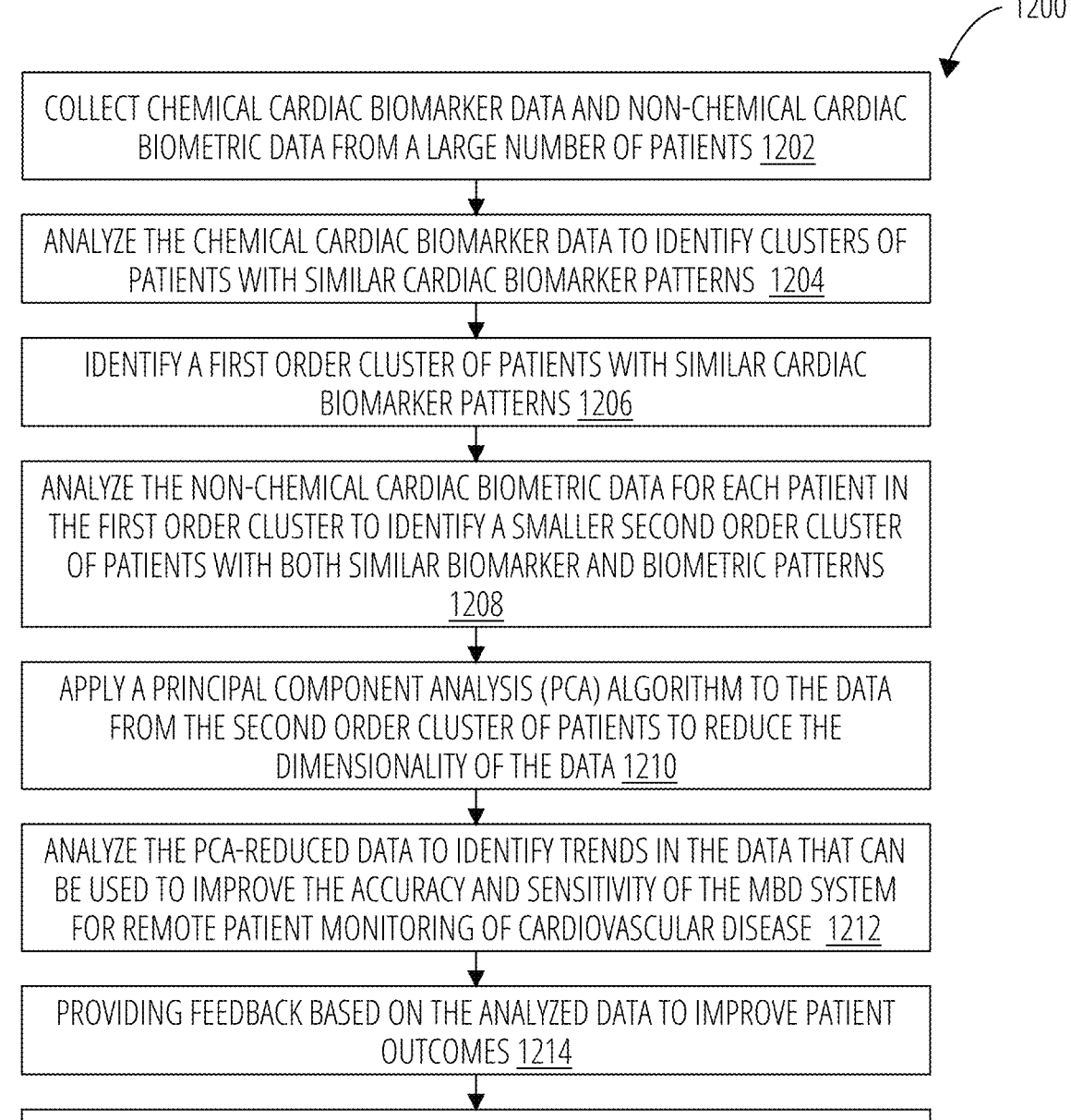

1200

COLLECT CHEMICAL CARDIAC BIOMARKER DATA AND NON-CHEMICAL CARDIAC BIOMETRIC DATA FROM A LARGE NUMBER OF PATIENTS 1202

ANALYZE THE CHEMICAL CARDIAC BIOMARKER DATA TO IDENTIFY CLUSTERS OF PATIENTS WITH SIMILAR CARDIAC BIOMARKER PATTERNS  1204

IDENTIFY A FIRST ORDER CLUSTER OF PATIENTS WITH SIMILAR CARDIAC BIOMARKER PATTERNS 1206

ANALYZE THE NON-CHEMICAL CARDIAC BIOMETRIC DATA FOR EACH PATIENT IN THE FIRST ORDER CLUSTER TO IDENTIFY A SMALLER SECOND ORDER CLUSTER OF PATIENTS WITH BOTH SIMILAR BIOMARKER AND BIOMETRIC PATTERNS 1208

APPLY A PRINCIPAL COMPONENT ANALYSIS (PCA) ALGORITHM TO THE DATA FROM THE SECOND ORDER CLUSTER OF PATIENTS TO REDUCE THE DIMENSIONALITY OF THE DATA 1210

ANALYZE THE PCA-REDUCED DATA TO IDENTIFY TRENDS IN THE DATA THAT CAN BE USED TO IMPROVE THE ACCURACY AND SENSITIVITY OF THE MBD SYSTEM FOR REMOTE PATIENT MONITORING OF CARDIOVASCULAR DISEASE  1212

PROVIDING FEEDBACK BASED ON THE ANALYZED DATA TO IMPROVE PATIENT OUTCOMES 1214

IMPLEMENT THE FEEDBACK TO IMPROVE THE MBD SYSTEM 1216

FIG. 12

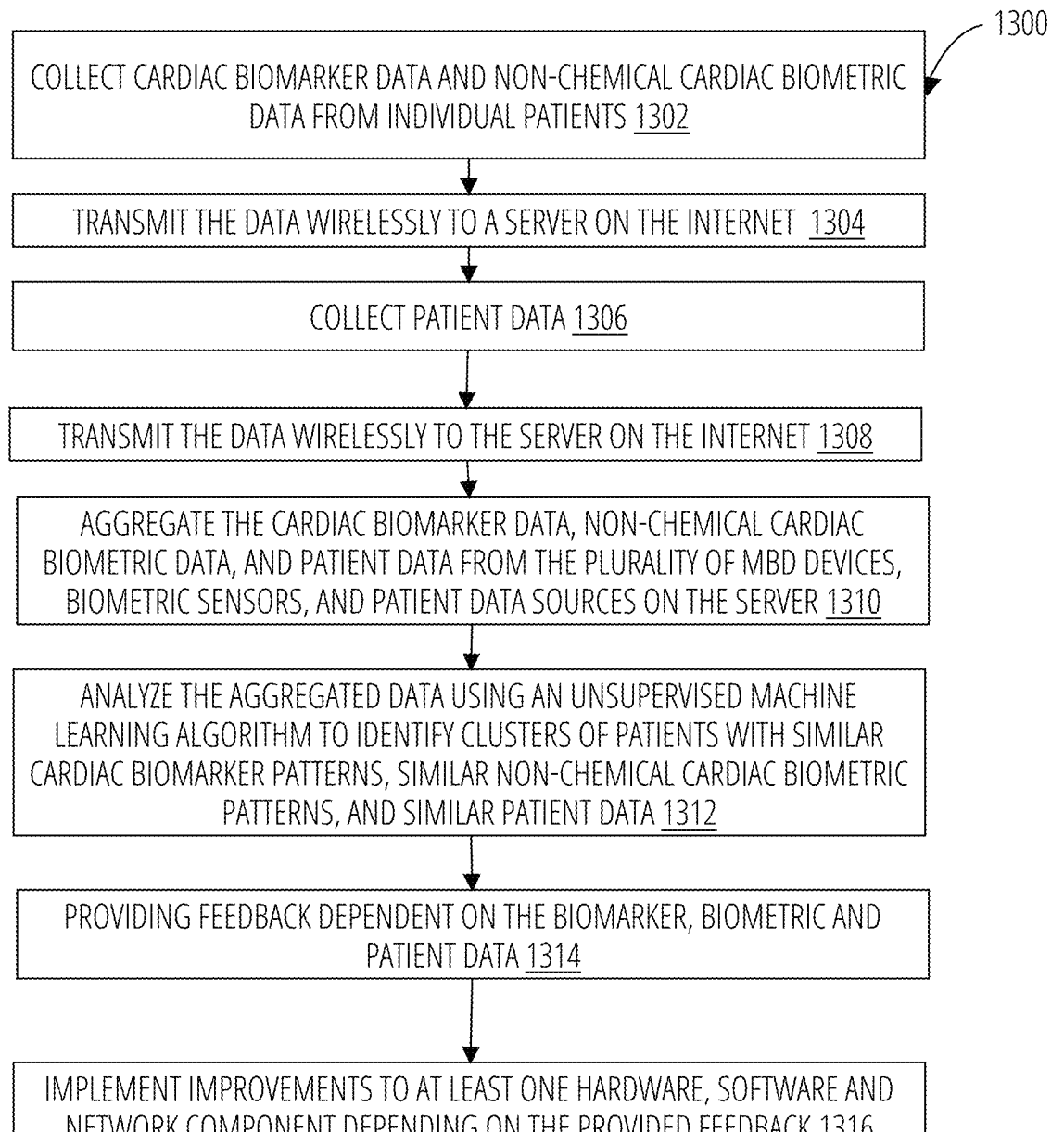

1300

COLLECT CARDIAC BIOMARKER DATA AND NON-CHEMICAL CARDIAC BIOMETRIC DATA FROM INDIVIDUAL PATIENTS 1302

TRANSMIT THE DATA WIRELESSLY TO A SERVER ON THE INTERNET 1304

COLLECT PATIENT DATA 1306

TRANSMIT THE DATA WIRELESSLY TO THE SERVER ON THE INTERNET 1308

AGGREGATE THE CARDIAC BIOMARKER DATA, NON-CHEMICAL CARDIAC BIOMETRIC DATA, AND PATIENT DATA FROM THE PLURALITY OF MBD DEVICES, BIOMETRIC SENSORS, AND PATIENT DATA SOURCES ON THE SERVER 1310

ANALYZE THE AGGREGATED DATA USING AN UNSUPERVISED MACHINE LEARNING ALGORITHM TO IDENTIFY CLUSTERS OF PATIENTS WITH SIMILAR CARDIAC BIOMARKER PATTERNS, SIMILAR NON-CHEMICAL CARDIAC BIOMETRIC PATTERNS, AND SIMILAR PATIENT DATA 1312

PROVIDING FEEDBACK DEPENDENT ON THE BIOMARKER, BIOMETRIC AND PATIENT DATA 1314

IMPLEMENT IMPROVEMENTS TO AT LEAST ONE HARDWARE, SOFTWARE AND NETWORK COMPONENT DEPENDING ON THE PROVIDED FEEDBACK 1316

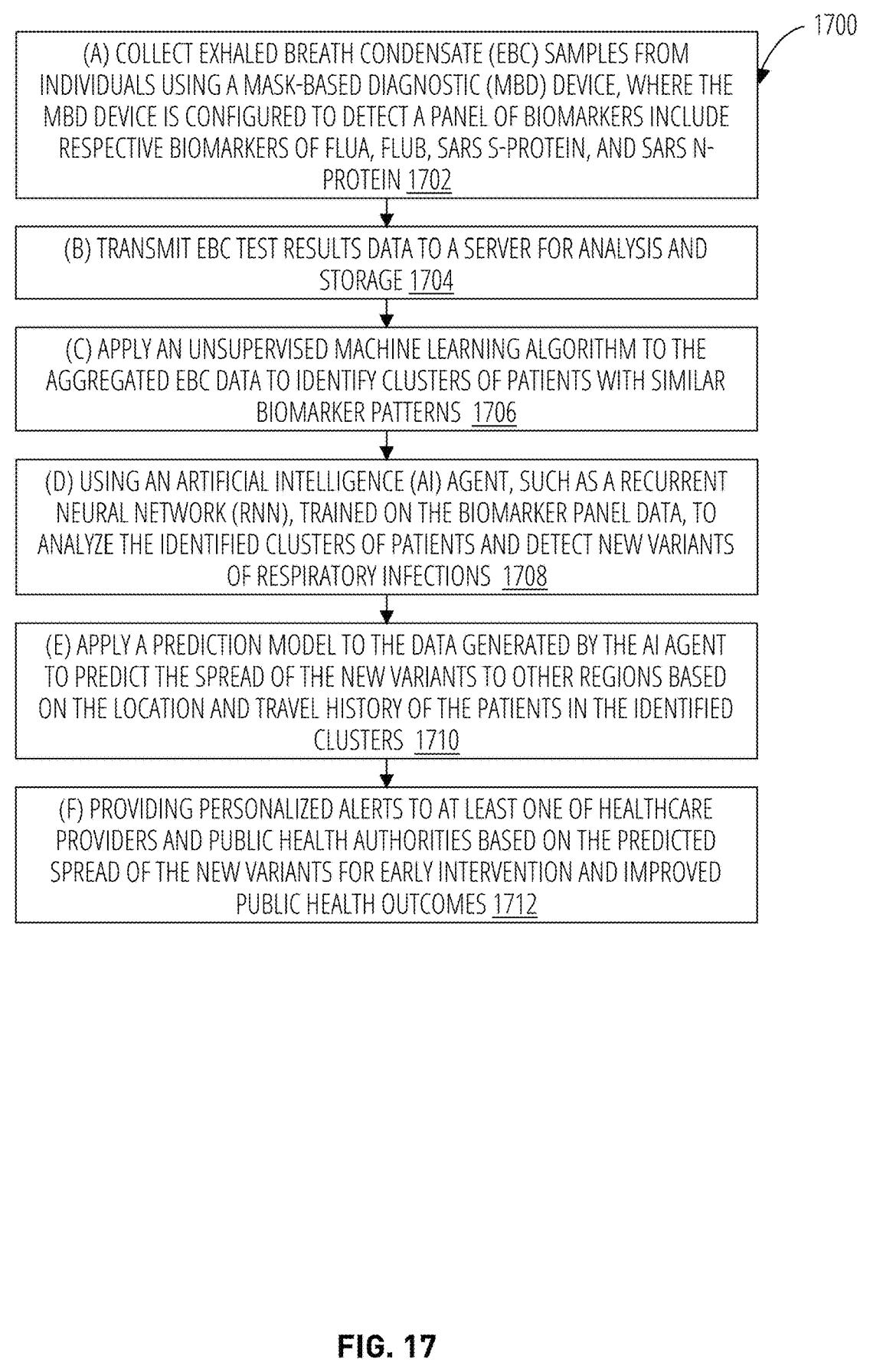

(A) COLLECT EXHALED BREATH CONDENSATE (EBC) SAMPLES FROM INDIVIDUALS USING A MASK-BASED DIAGNOSTIC (MBD) DEVICE, WHERE THE MBD DEVICE IS CONFIGURED TO DETECT A PANEL OF BIOMARKERS INCLUDE RESPECTIVE BIOMARKERS OF FLUA, FLUB, SARS S-PROTEIN, AND SARS N-PROTEIN 1702

(B) TRANSMIT EBC TEST RESULTS DATA TO A SERVER FOR ANALYSIS AND STORAGE 1704

(C) APPLY AN UNSUPERVISED MACHINE LEARNING ALGORITHM TO THE AGGREGATED EBC DATA TO IDENTIFY CLUSTERS OF PATIENTS WITH SIMILAR BIOMARKER PATTERNS 1706

(D) USING AN ARTIFICIAL INTELLIGENCE (AI) AGENT, SUCH AS A RECURRENT NEURAL NETWORK (RNN), TRAINED ON THE BIOMARKER PANEL DATA, TO ANALYZE THE IDENTIFIED CLUSTERS OF PATIENTS AND DETECT NEW VARIANTS OF RESPIRATORY INFECTIONS 1708

(E) APPLY A PREDICTION MODEL TO THE DATA GENERATED BY THE AI AGENT TO PREDICT THE SPREAD OF THE NEW VARIANTS TO OTHER REGIONS BASED ON THE LOCATION AND TRAVEL HISTORY OF THE PATIENTS IN THE IDENTIFIED CLUSTERS 1710

(F) PROVIDING PERSONALIZED ALERTS TO AT LEAST ONE OF HEALTHCARE PROVIDERS AND PUBLIC HEALTH AUTHORITIES BASED ON THE PREDICTED SPREAD OF THE NEW VARIANTS FOR EARLY INTERVENTION AND IMPROVED PUBLIC HEALTH OUTCOMES 1712

FIG. 17

MASK-BASED DIAGNOSTIC UTILIZING AI ALGORITHMS FOR IMPROVED PATIENT OUTCOMES

This application is a continuation of U.S. patent application Ser. No. 18/301,967, filed 2023 Apr. 17, and entitled "Mask-Based Diagnostic Utilizing AI Algorithms for Improved Patient Outcomes," the teachings of which are incorporated herein by reference.

BACKGROUND

The exemplary and non-limiting embodiments relate generally to diagnostic systems, methods, devices and computer programs and, more specifically, relate to digital and analog diagnostic devices for detecting a biomarker of a biological agent such as a coronavirus, lung cancer, tuberculosis, asthma, and other respiratory ailments and conditions, and/or blood borne biomarkers and other biomarkers that are present in the exhaled breath of a test subject such as host-generated biomarkers of cardiac diseases.

The present invention also pertains to a device architecture, specific-use applications, and computer algorithms used to detect biometric parameters for the treatment and monitoring of physiological conditions in humans and animals by testing for biomarkers in exhaled breath, sweat, blood, urine, feces, gastro-intestinal lavage, interstitial fluid, mucus, saliva, or other bodily fluid.

This section is intended to provide a background or context to the exemplary embodiments of the invention as recited in the claims. The description herein may include concepts that could be pursued but are not necessarily ones that have been previously conceived, implemented or described.

Therefore, unless otherwise indicated herein, what is described in this section is not prior art to the description and claims in this application and is not admitted to being prior art by inclusion in this section.

Testing for biomarkers that indicate exposure, infection, progression and recovery from a disease condition, can be used to screen individuals for infection. Especially for diseases caused by novel pathogens like the recent SARS-CoV-2 virus, testing can help slow the spread of the virus and detect new variants of the virus in a population. For example, protein and RNA testing for active virus shows who is currently contagious. Antibody testing can be used to find the members of a population that have recovered from the virus.

Diagnostics of an infection, such as SARS-CoV-2 infection, using real-time reverse-transcription polymerase chain reaction (RT-PCR) on nasopharyngeal swabs is now well-established, with saliva-based testing being lately more widely implemented for being more adapted for self-testing approaches. The procedure to obtain nasal swab samples is not only uncomfortable, but also often requires specialized personnel with risk of contaminating the person performing the test. Saliva tests have the advantage of being simpler to perform, less invasive with limited risks and RT-PCR on saliva specimens has becoming more widely implemented. The viscose nature of saliva together with the presence of saliva proteases, responsible for the proteolytic activity of saliva, make the direct application of saliva samples challenging. It is well known that the major mechanisms of COVID-19 spread are airborne and contact infections primarily due to aerosol droplets expelled from the lungs and airways of infected persons. There is therefore a growing need for sample collection by patients themselves and a simple to use testing system that can detect a target biomarker indicative of a pathogenic infection from a biosample obtained from the lungs and airways.

The diagnosis of certain medical conditions, such as cardiovascular disease, often requires the monitoring of specific biomarkers present in biological samples, such as exhaled breath condensate (EBC). EBC samples contain a complex mixture of chemicals and biomolecules, including potential biomarkers of disease. The detection and quantification of these biomarkers can provide valuable diagnostic information. However, the collection and analysis of EBC samples is challenging, as the samples are often low in volume and the biomarkers of interest may be present in low concentrations.

Mask-based diagnostic (MBD) systems have been developed to address some of the challenges associated with the collection and analysis of EBC samples. MBDs are face masks that contain an exhaled breath condensate (EBC) collector, which converts breath vapor into an EBC liquid sample. The EBC sample can be analyzed for specific biomarkers of interest using a biosensor integrated into the mask. However, the analysis of EBC samples collected by MBDs can still be challenging due to the low concentrations of biomarkers and potential confounding factors present in the sample.

To address these challenges, there is a need for a medical monitoring system that can collect and analyze EBC samples using MBDs, along with additional biometrics. As an example, cardiovascular disease patients generate host-based cardiac biomarkers that are found in EBC. A medical monitoring system that addresses the challenges above utilizes these host-based biomarkers with additional relevant biometrics, such as heart rate and skin temperature obtained from biometric sensors and can apply artificial intelligence (AI) algorithms to identify patterns in the data and provide feedback to improve patient outcomes. Such a system could enable remote monitoring of patients with cardiovascular disease, allowing for early detection and intervention to improve patient outcomes.

BRIEF SUMMARY

In one aspect, a method, includes collecting at least one of individual patient chemical biomarker data and non-chemical biometric data using a remote patient monitoring system, transmitting the data to a remote server, aggregating the data on the remote server, analyzing the aggregated data using an AI agent to identify patterns and trends in the data, generating feedback based on the identified pattern and trends, providing feedback to improve efficacy of the remote patient monitoring system, and implementing the feedback to improve at least one hardware, software and networking component of the remote patient monitoring system.

In one aspect, a method for remote patient monitoring of cardiovascular disease, includes collecting cardiac biomarker data from individual patients using a plurality of MBD devices and transmitting the data wirelessly to a server on the internet. Collecting non-chemical cardiac biometric data from individual patients using a plurality of biometric sensors and transmitting the data wirelessly to the server on the internet. Aggregating the cardiac biomarker data and non-chemical cardiac biometric data from the plurality of MBD devices and biometric sensors on the server. Analyzing the aggregated data using an unsupervised machine learning algorithm to identify clusters of patients with similar cardiac biomarker patterns and similar non-chemical cardiac biometric patterns. Applying a principal component analysis (PCA) algorithm to the data from the first order clusters of patients to reduce the dimensionality of the data and identify a second order of clusters of patients with similar cardiac biomarker patterns and similar non-chemical cardiac biometric patterns.

In one aspect, a system for remote patient monitoring of cardiovascular disease, includes: a plurality of MBD devices configured to collect cardiac biomarker data from individual patients and transmit the data wirelessly to a server on the internet; a plurality of biometric sensors configured to collect non-chemical cardiac biometric data from the individual patients and transmit the data wirelessly to the server on the internet; a server configured to receive and aggregate the cardiac biomarker data and non-chemical cardiac biometric data from the plurality of MBD devices and biometric sensors; an unsupervised machine learning algorithm configured to analyze the aggregated data to identify clusters of patients with similar cardiac biomarker patterns and similar non-chemical cardiac biometric patterns; a principal component analysis (PCA) algorithm configured to reduce the dimensionality of the data from the first order clusters of patients and identify a second order of clusters of patients with similar cardiac biomarker patterns and similar non-chemical cardiac biometric patterns.

In one aspect, a system for predicting future cardiac events in a patient, includes: a Mask-Based Diagnostic (MBD) device configured to collect exhaled breath condensate (EBC) and detect cardiac biomarkers using multiplexed biosensors and synthetic bioreceptors; a smartphone APP in communication with the MBD device, the APP configured to receive and analyze the biomarker data generated by the MBD device, an artificial intelligence (AI) agent, such as a Recurrent Neural Network (RNN), trained to analyze the biomarker data and predict the likelihood of future cardiac events for the individual patient, and a communication module configured to provide personalized alerts to the patient or their healthcare provider based on the predicted likelihood of future cardiac events, for early intervention and improved patient outcomes.

In one aspect, a system for remote patient monitoring of cardiac biomarkers using an MBD includes a plurality of MBD devices configured to collect cardiac biomarker data from individual patients and transmit the data wirelessly to a server on the internet, a server configured to receive and aggregate the cardiac biomarker data from the plurality of MBD devices and apply an unsupervised machine learning algorithm to identify clusters of patients with similar cardiac biomarker patterns, and an artificial intelligence agent, such as GBT, configured to analyze the cardiac biomarker data from the identified clusters of patients and identify trends in the data that can be used to improve the accuracy of the MBD system for remote patient monitoring of cardiac biomarkers.

In one aspect, a method for improving a diagnostic system for remote patient monitoring of cardiac biomarkers, includes collecting cardiac biomarker data from a plurality of patients using MBD devices and transmitting the data wirelessly to a server on the internet, aggregating the cardiac biomarker data from the plurality of patients and identifying clusters of patients with similar cardiac biomarker patterns using an unsupervised machine learning algorithm, analyzing the cardiac biomarker data from the identified clusters of patients using an artificial intelligence agent, such as GBT, to identify trends in the data, and using the identified trends in the data to develop and implement improvements to the MBD system for remote patient monitoring of cardiac biomarkers.

In one aspect, a method for improving a mask-based diagnostic (MBD) system, includes collecting chemical cardiac biomarker data and non-chemical cardiac biometric data from a large number of patients using an MBD device to collect the biomarker data and at least biometric sensor to collect the biometric data, analyzing the chemical cardiac biomarker data to identify clusters of patients with similar cardiac biomarker patterns, identifying a first order cluster of patients with similar cardiac biomarker patterns, analyzing the non-chemical cardiac biometric data for each patient in the first order cluster to identify a smaller second order cluster of patients with both similar biomarker and biometric patterns, applying a principal component analysis (PCA) algorithm to the data from the second order cluster of patients to reduce the dimensionality of the data, analyzing the PCA-reduced data to identify trends in the data that can be used to improve the accuracy of the MBD system for remote patient monitoring of cardiovascular disease, providing feedback based on the analyzed data to improve patient outcomes, and implementing the feedback to improve the MBD system.

In one aspect, a method for improving patient outcomes in remote patient monitoring of cardiac biomarkers, includes a) collecting cardiac biomarker data from a patient using a Mask-Based Diagnostic (MBD) device and transmitting the data wirelessly to a server on the internet, b) analyzing the cardiac biomarker data using an artificial intelligence (AI) agent to identify trends in the data and predict the likelihood of future cardiac events for the individual patient, and c) providing personalized alerts to the patient or their healthcare provider based on the predicted likelihood of future cardiac events, for early intervention and improved patient outcomes.

In one aspect, a method for improving the outcomes of cardiac patients, includes a. Collecting chemical cardiac biomarker data and non-chemical cardiac biometric data from a plurality of patients using a Mask-Based Diagnostic (MBD) device and at least one biometric sensor, b. Transmitting the biomarker and biometric data wirelessly to a server on the internet, c. Aggregating the biomarker and biometric data from the plurality of patients and applying an unsupervised machine learning algorithm to identify clusters of patients with similar cardiac biomarker and biometric patterns, d. Analyzing the identified clusters of patients using an artificial intelligence (AI) agent, such as a Recurrent Neural Network (RNN), to predict the likelihood of future cardiac events for individual patients, e. Providing personalized alerts to the patient or their healthcare provider based on the predicted likelihood of future cardiac events, for early intervention and improved patient outcomes, f. Analyzing the identified clusters of patients using a PCA algorithm to identify a second order of clusters of patients with both similar biomarker and biometric patterns, g. Analyzing the second-order clusters of patients for trends in the data that can be used to improve the accuracy and sensitivity of the MBD system for remote patient monitoring of cardiovascular disease, h. Implementing the feedback to improve the MBD system, and i. Applying an applied treatment to the patients based on the detected changes in the biomarker and biometric data and evaluating the effectiveness of the treatment using an AI algorithm.

In one aspect, a method for remote patient monitoring of cardiovascular disease, includes collecting cardiac biomarker data from individual patients using a plurality of MBD devices and transmitting the data wirelessly to a server on the internet. Collecting non-chemical cardiac biometric data from individual patients using a plurality of biometric sensors and transmitting the data wirelessly to the server on the internet. Aggregating the cardiac biomarker data and non-chemical cardiac biometric data from the plurality of MBD devices and biometric sensors on the server. Analyzing the aggregated data using an unsupervised machine learning algorithm to identify clusters of patients with similar cardiac biomarker patterns and similar non-chemical cardiac biometric patterns. Applying a principal component analysis (PCA) algorithm to the data from the first order clusters of patients to reduce the dimensionality of the data and identify a second order of clusters of patients with similar cardiac biomarker patterns and similar non-chemical cardiac biometric patterns.

In one aspect, a method for detecting and predicting the spread of respiratory infections, includes (a) collecting exhaled breath condensate (EBC) samples from individuals using a Mask-Based Diagnostic (MBD) device, where the MBD device is configured to detect a panel of biomarkers including respective biomarkers of Flu A, Flu B, SARS S-protein, and SARS N-protein, (b) transmitting the collected EBC samples to a server for analysis and storage, (c) applying an unsupervised machine learning algorithm to the aggregated EBC data to identify clusters of patients with similar biomarker patterns, (d) using an artificial intelligence (AI) agent, such as a Recurrent Neural Network (RNN), trained on the biomarker panel data, to analyze the identified clusters of patients and detect new variants of respiratory infections, (e) applying a prediction model to the data generated by the AI agent to predict the spread of the new variants to other regions based on the location and travel history of the patients in the identified clusters, and (f) providing personalized alerts to at least one of healthcare providers and public health authorities based on the predicted spread of the new variants for early intervention and improved public health outcomes.

In one aspect, a method for detecting and predicting the spread of respiratory infections, includes (a) collecting exhaled breath condensate (EBC) samples from individuals using a Mask-Based Diagnostic (MBD) device, where the MBD device is configured to detect a panel of biomarkers including respective biomarkers of FluA, FluB, SARS S-protein, and SARS N-protein, (b) transmitting the collected EBC samples to a server for analysis and storage, (c) applying an unsupervised machine learning algorithm to the aggregated EBC data to identify clusters of patients with similar biomarker patterns, (d) using an artificial intelligence (AI) agent, such as a Recurrent Neural Network (RNN), trained on the biomarker panel data, to analyze the identified clusters of patients and detect new variants of respiratory infections, (e) applying a prediction model to the data generated by the AI agent to predict the spread of the new variants to other regions based on the location and travel history of the patients in the identified clusters, and (f) providing personalized alerts to at least one of healthcare providers and public health authorities based on the predicted spread of the new variants for early intervention and improved public health outcomes.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 1 illustrates a flowchart in accordance with one embodiment.

FIG. 2 illustrates a flowchart for improving the outcomes of cardiac patients, in accordance with one embodiment.

FIG. 9 illustrates a routine 900 for improving the accuracy of the MBD system for remote patient monitoring of cardiac biomarkers, in accordance with one embodiment.

FIG. 10 is a flowchart showing how MBD test results data can be collected and transmitted for AI analysis for improving patient outcomes using remote patient monitoring.

FIG. 11 shows a patient wearing an MBD 1102 for obtaining chemical biomarker test data from EBC and a wrist cuff biometric sensor 1104 for obtaining non-chemical biometric data.

FIG. 12 is a flowchart showing how the analysis of chemical biomarker data and non-chemical biometric data can improve the mask-based diagnostic (MBD) system.

FIG. 13 is a flow chart showing the use of collected patient data accumulated along with chemical biomarker and non-chemical biosensor data.

FIG. 17 is a flowchart showing how the MBD can be used for detecting and predicting the spread of respiratory infections.

DETAILED DESCRIPTION

Figures 3, 4:
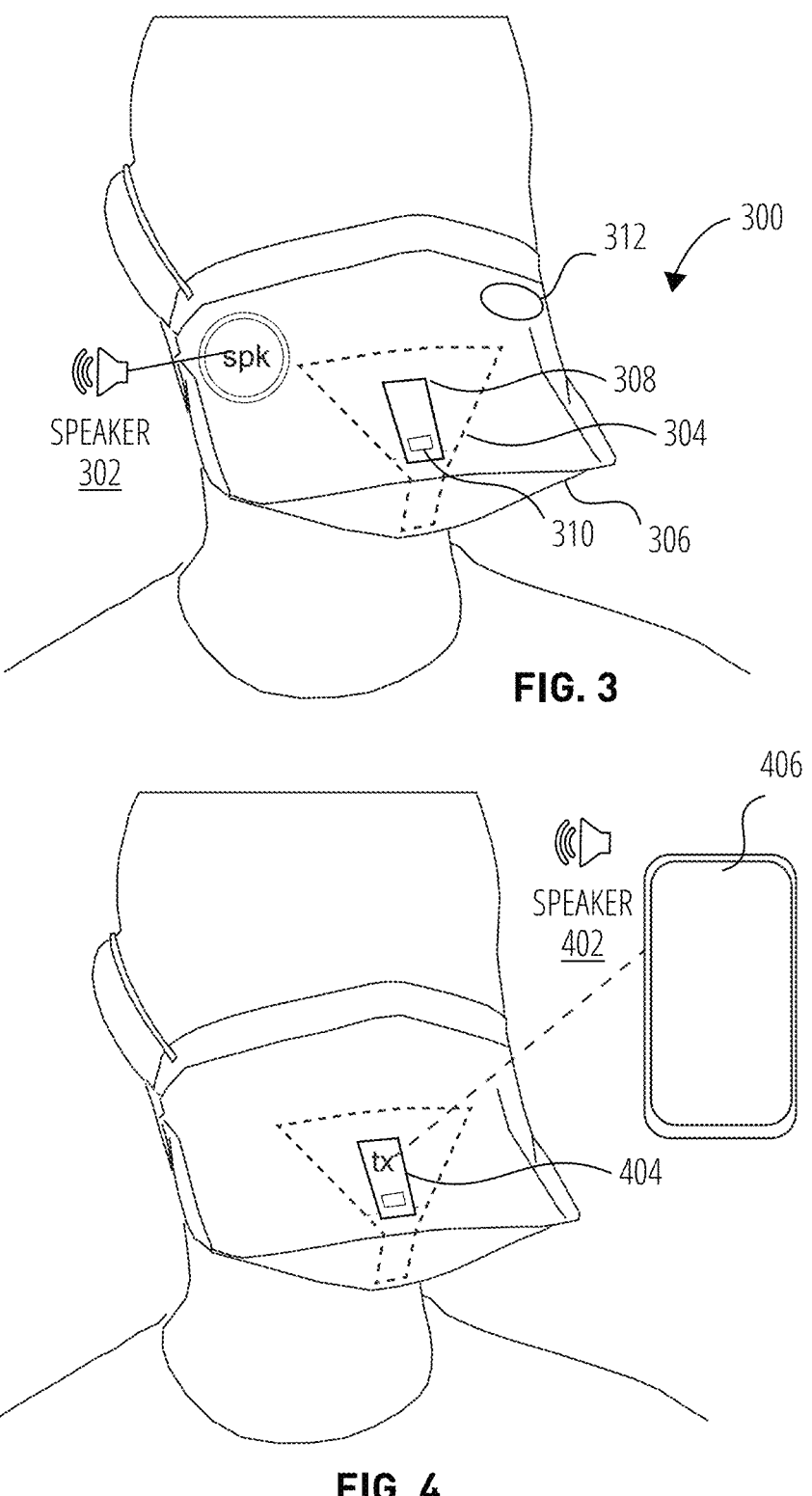
FIG. 3 illustrates an MBD with a self-contained user interface.
FIG. 4 illustrates another version of the MBD with a Bluetooth wireless transmitter onboard the MBD.

Below are provided further descriptions of various non-limiting, exemplary embodiments. The exemplary embodiments of the invention, such as those described immediately below, may be implemented, practiced or utilized in any combination (e.g., any combination that is suitable, practicable and/or feasible) and are not limited only to those combinations described herein and/or included in the appended claims.

The word "exemplary" is used herein to mean "serving as an example, instance, or illustration." Any embodiment described herein as "exemplary" is not necessarily to be construed as preferred or advantageous over other embodiments. In any case, all of the embodiments described in this Detailed Description are exemplary embodiments provided to enable persons skilled in the art to make or use the invention and not to limit the scope of the invention which is defined by the claims.

Many configurations, embodiments, methods of manufacture, algorithms, electronic circuits, microprocessors, static and dynamic Memory and computer software product combinations, networking strategies, database structures and uses, and other aspects are disclosed herein for a diagnostic or testing platform, devices, methods and systems that have a number of medical and non-medical uses.

Although embodiments are described herein for detection of biomarkers of SARS-CoV-2 virus, the systems, methods and apparatus described are not limited to any particular virus or disease, or just limited to biological use-cases. In most instances, where the term virus or COVID-19 is used, any other health or fitness related biomarker could be used instead. The description here and the drawings and claims are therefore not intended to be limited in any way to virus detection, the inventions described and claimed can be used for many diseases and related biomarkers or target molecules/analytes including lung cancer, diabetes, asthma, tuberculosis, environmental exposures, glucose, lactate, blood borne diseases and other ailments or indications of the health of the test subject. Further, the electronic biosensor, test systems, uses and methods of manufacturing described herein are not limited to the use of exhaled breath condensate. Wastewater, potable water, environmental quality samples, ambient samples and any bodily fluid can be used as the test sample. The use of aptamers and engineered capture molecules, in particular, make the inventive sensor widely useful because of the nature of engineered capture molecules such as aptamers, nanoCLAMPs, nano-bodies, engineered anti-bodies, etc., being adaptable by specific engineering design and selection to have a binding affinity that is tailored to a corresponding target analyte. Therefore, the descriptions of innovations are not intended to be limited to a particular use-case, sample medium, capture molecule, biomarker or analyte.

As described herein, the term antibody, aptamer, engineered antibody, bioreceptor or capture molecule is used interchangeably. In some instances, a specific type of capture molecule may be described. In the case of a lateral flow assay (LFA) type testing system, biomarkers in the sample are bound by the capture molecules which are coupled to a detector reagent. As the sample passes through the area where the capture molecule is disposed, a biomarker detector reagent complex is trapped, and a color develops that is proportional to the concentration or amount biomarker present in the sample. In the case of an electronic or electrochemical testing system, the captured biomarker causes a detectable change in a signal obtained, typically through an electrical connection with two or more electrodes.

The mask-based diagnostic device is a diagnostic tool designed to be worn as a face mask, which includes an exhaled breath condensate (EBC) collector and an EBC testing unit. The EBC collector has a condensate forming surface that converts exhaled breath vapor into an EBC liquid sample, which contains the target molecule that the device is designed to detect. The EBC collector is cooled before use so that the condensate forming surface is at a condensation forming temperature that is lower than the confined environment temperature inside of the face mask. The EBC testing unit comprises a printed circuit board supporting a semiconductor packaged electronic biosensor in electrical communication with power, analysis and communications electronics, a fluid conductor for conducting the EBC sample to the electronic biosensor, the analysis electronics for detecting the target molecule dependent on an electrical signal received from the electronic biosensor, and the communications electronics for communicating the detection of the target molecule. The printed circuit board may include a fluid detector onboard the printed circuit board for detecting at least one of a start of fluid conduction through the fluid conductor in a flow path before the electronic biosensor and an end of fluid conduction in the flow path after the electronic biosensor.

The mask-based diagnostic device also includes several additional features, such as a fluid conductor that is designed to reduce adhesion of the target molecule to limit target molecules removed from the portion of the EBC sample that flows in the flow path while the target molecule is carried along with the EBC sample to the electronic biosensor. The condensate forming surface of the EBC collector comprises a low surface energy material to reduce adhesion of the target molecule to limit target molecules removed from the collected EBC sample. In addition, the device includes a super absorbent polymer (SAP) that is provided in the flow path before the electronic biosensor for selectively adsorbing water from the EBC sample and concentrating the target molecule in a portion of the EBC sample that reaches the electronic biosensor.

The thermal mass of the EBC collector is disposed between two sheets of adhesive, where one of the adhesive sheets supports a low surface energy sheet comprising the condensate forming surface, and the other adhesive sheet comprises a support member for supporting the EBC collector on the inside of the face mask. The device further includes a collection pool for receiving the EBC, and the fluid conductor conducts the EBC from the collection pool to the EBC testing unit.

The mask-based diagnostic device also has removable and recyclable components, which include a support member configured and dimensioned to removably fit into a face mask, an EBC collector supported on the support member and an attachment member for removably attaching the support member and EBC collector to the inside of the face mask.

Overall, the mask-based diagnostic device is a novel and innovative diagnostic tool that allows for the detection of target molecules in exhaled breath condensate (EBC) non-invasively obtained in a confined local environment, such as a face mask.

In a deployment for testing a cohort of patients with a similar disease or condition, such as recovering from a recent heart attack, multiple MBD devices collect cardiac biomarker data from individual patients and transmit the data from each patient wirelessly to a server on the internet. The server receives and aggregates the cardiac biomarker data from the plurality of MBD devices and applies an unsupervised machine learning algorithm to identify clusters of patients with similar cardiac biomarker patterns and possibly patient demographics. This would allow for the identification of groups of patients who share similar characteristics and may benefit from similar interventions.

Once these clusters of patients are identified, an artificial intelligence agent (such as GBT) can analyze the cardiac biomarker data from the identified clusters of patients to identify trends in the data that can be used to improve the accuracy of the MBD system for remote patient monitoring of cardiac biomarkers. For example, the AI agent can identify certain biomarkers concentrations for patients with the demographic categories, such as same age, sex, etc., that are particularly predictive of future heart events and adjust the monitoring protocols accordingly, for example, more or less frequent testing using the MBD.

The system could provide feedback to healthcare providers and patients in several ways. Healthcare providers could be alerted to patients who are at higher risk of future heart events based on the analysis of their cardiac biomarker data. This could allow for early intervention and potentially improve patient outcomes. Using the wireless smartphone user interface, or spoken word notifications, patients themselves could also receive feedback and be encouraged to make lifestyle changes to improve their heart health based on the analysis of their data.

Overall, the system can help to identify patterns in cardiac biomarker data that would be difficult for healthcare providers to identify on their own. This could potentially lead to more targeted and effective interventions for patients who have had a heart attack.

The trends in the data that can be identified by the AI agent can include patterns in the cardiac biomarker levels of patients in different clusters, such as correlations between the levels of different biomarkers, changes in biomarker levels over time, and how these patterns differ between patients with different demographics or health histories. The system can also be used to identify trends in patient outcomes, such as the likelihood of readmission to the hospital or the development of complications based on the patterns of biomarker levels over time. By identifying these trends, the system can potentially provide feedback to improve the accuracy of future generations of the MBD system, as well as to help clinicians make more informed decisions about patient care. The data can also include self-reported patient information indicating usability of the MBD, doctor reported information such as value and desired thresholds for alerts, etc. The patient and doctor reported information can be captured via the patient's cellphone (e.g., patient questionnaire) or a doctor's desktop computer dashboard (tracking multiple patients).

Based on the identified trends, the manufacturer of the MBD can improve the design of the device in several ways, such as:

Improving the accuracy of the MBD: The identified trends can be used to modify the sensors and data collection mechanisms of the MBD to improve the accuracy of the device in detecting cardiac biomarkers. For example, the usefulness of certain biomarkers that are more strongly correlated with cardiac events can be identified helping to adjust the makeup of a panel of multiple biomarkers tested from the EBC sample. As patterns emerge from the AI-analyzed data, the biomarkers that are tested for can be adjusted depending on factors such as patient demographics, severity of the disease, progress and disease recovery, hereditary and patient history, body mass index, medications, etc.

Modifying the form factor and use of the MBD: If the data suggests that patients are not wearing the MBD as often as they should, the form factor of the device can be modified to make it more comfortable and convenient to wear, or easy to put one.

Enhancing the user interface: If the data suggests that patients are having difficulty using the MBD, the user interface can be improved to make it more intuitive and user-friendly. For example, simplified instructions or additional visual cues can be added to guide users through the data collection process.

Improving the battery life: If the data suggests that the battery life of the MBD is too short, the electronic circuit can be modified to improve battery efficiency or add a larger battery to extend the life of the device.

Providing additional resources and support: If the data suggests that patients are having difficulty understanding their biomarker data or interpreting the results, additional resources and support can be provided to help patients understand and use the data to manage their condition more effectively. For example, educational materials can be developed or access provided to telehealth consultations with healthcare professionals.

Including additional biometrics such as continuously monitored heart rate and skin temperature can provide more comprehensive and real-time data to the AI agent for analysis, which can further improve the accuracy of the MBD system for remote patient monitoring of cardiac biomarkers.

For example, the AI agent can analyze the correlation between changes in the patient's heart rate and skin temperature and the level of the cardiac biomarker in the patient's blood. If a particular pattern emerges where a significant change in the patient's heart rate and skin temperature is consistently observed shortly before an increase in a cardiac biomarker level, this could be an indication of a potential heart attack risk. The AI agent could then provide feedback to the patient and their healthcare provider to take preventive measures, such as adjusting medication dosage, dietary changes or increasing exercise, to reduce the risk of a heart attack.

Moreover, the AI agent could also analyze the correlation between the patient's biometrics and their lifestyle habits, such as exercise and diet, accessing data obtained from other APPs or data sources, such as the user's cellphone accelerometer data, other APPs) to identify specific behaviors that may contribute to changes in the patient's cardiac biomarker levels. This information could be used to provide personalized recommendations to the patient and their healthcare provider on how to modify their behavior to improve their cardiac health.

The inclusion of additional biometrics along with the cardiac biomarker data can provide a more holistic view of the patient's health status, enabling the AI agent to provide more accurate and personalized feedback to improve patient outcomes.

The MBD can also be provided with accessibility features that are suitable for self-testing by individuals with visual or physical impairments. The user only needs to wear the mask and breathe normally for about 10 minutes. The MBD includes electronics that generate visual and audible signals to provide automatic readout of the test results. The use of the MBD is as easy as putting on a conventional face mask, and the user is provided with simple spoken instructions to follow to perform the test.

The EBC biosample tested using a graphene-based biosensor offers synergistic advantages over all other available OTC and laboratory tests. The liquid biosample is mostly water and presents a very clean and immediate snapshot of the infection. The MBD's accessibility characteristics include very elegant usability features and automatic readout in the form of visual and audible signals.

FIG. 1 shows a method in accordance with a non-limiting embodiment that involves the collection of individual patient chemical biomarker data and non-chemical biometric data using a remote patient monitoring system. The data is then transmitted to a remote server where it is aggregated, analyzed using an AI agent to identify patterns and trends, and generate feedback based on the identified pattern and trends. The feedback is provided to improve the efficacy of the remote patient monitoring system, and the feedback is implemented to improve at least one hardware, software, and networking component of the remote patient monitoring system.

As an example, a software improvement can include automatically changing a user-interface to provide an indication to the individual patient to change the time or frequency of use of the chemical biomarker testing system and the biometric detecting system used by the remote patient monitoring system. As another example, the user interface may also provide reminders to the individual patient to perform tests at specific times of the day or on certain days of the week and/or reminders for taking medications or other therapies.

A hardware improvement can include changing a biosensor to detect a new chemical biomarker. For example, a new capture molecule for the biosensor can be developed that can detect an additional biomarker that was previously not measured, providing more comprehensive data.

A network improvement can include changing a remote server to include a new AI agent. For example, an updated AI agent can be automatically installed on the remote server, which may improve the accuracy and efficiency of data analysis and feedback generation.

The MBD system can utilize AI-agents to improve patient outcomes, lower payer costs, and improve doctor and patient engagement. By collecting individual patient biomarker and biometric data using a remote patient monitoring system, the MBD system can track a patient's health status over time and identify potential health concerns before they become more serious.

By transmitting this data to a remote server and aggregating it, the MBD system can analyze the data using an AI agent to identify patterns and trends. Based on this analysis, the system can generate feedback to improve the efficacy of the remote patient monitoring system. For example, if the AI agent detects a trend in the data indicating that patients are experiencing adverse effects from a certain medication, the system can generate automatic alerts indicating the adverse effects and suggesting a change in medication or dosage, or consultation with a doctor.

By implementing this feedback to improve the hardware, software, and networking components of the remote patient monitoring system, the MBD system can improve patient outcomes and lower payer costs by reducing length of hospital stays and readmissions, emergency room visits, laboratory tests, and unnecessary medical procedures. Additionally, by providing doctors and patients with actionable feedback, the MBD system can improve engagement and promote more proactive management of chronic conditions, ultimately leading to better patient outcomes.

In block 102, at least one of individual patient chemical biomarker data and non-chemical biometric data is collected using a remote patient monitoring system. In block 104, the data is transmitted to a remote server. In block 106, the data is aggregated on the remote server. In block 108, the aggregated data is analyzed using an AI agent to identify patterns and trends in the data. In block 110, feedback is generated based on the identified pattern and trends. In block 112, the feedback is provided, for example to the manufacturer of the MBD system or as automatically implementable actions to improve efficacy of the remote patient monitoring system. In block 114, the feedback is implemented to improve at least one hardware, software and networking component of the remote patient monitoring system.

The AI analysis of the collected data can identify patterns and trends that indicate areas for potential improvement in the hardware component of the remote patient monitoring system. For example, the AI agent may identify that certain sensors are consistently providing data with high variability or that certain components are frequently failing.

Based on this feedback, a design of experiments (DOE) can be created to systematically test and optimize various hardware features. The DOE can be designed to test one variable at a time, or multiple variables in combination, to identify the optimal configuration for the hardware feature being tested.

A DOE virtual model can be automatically performed by an AI-agent using the aggregated biomarker, biometric, and other patient data obtained using the MBD system. DOE is a systematic method to determine the relationship between variables and identify the most critical variables that affect a particular outcome. In the context of remote patient monitoring of cardiovascular disease, DOE can help optimize the remote patient monitoring system to improve patient outcomes.

The AI-agent can use the aggregated data to identify potential variables that may affect patient outcomes, such as the frequency of testing, the type of biomarker detected, the type of biosensor used, the time of day when testing is performed, and the age of the patient. The AI-agent can then perform a DOE model to determine the impact of each variable on patient outcomes, such as the incidence of cardiac events, the time to diagnosis, and the cost of care.

The DOE model can be designed to test various combinations of variables to determine the optimal settings for the remote patient monitoring system. For example, the AI-agent can filter the aggregated data so that the virtual model can test different frequencies of testing for each biomarker, different types of biosensors for each biomarker, and different times of day for testing. The AI-agent can also vary the age of patients, the severity of their disease, and other factors to determine the impact of these variables on patient outcomes.

The output of the DOE model can provide valuable insights to optimize the remote patient monitoring system. For instance, the model may reveal that increasing the frequency of testing for a particular biomarker improves patient outcomes, or that changing the biosensor to detect a new biomarker improves the accuracy of diagnoses.

The virtual DOE model can be used to develop a real-world DOE to physically refine the actual remote patient monitoring system to improve patient outcomes, reduce costs, and enhance patient satisfaction.

For instance, if the AI analysis and virtual DOE model indicates that a biometric sensor in the remote patient monitoring system is producing data with high variability, a DOE can be designed to test various configurations of the type of sensor to identify the optimal configuration. This could include testing different sensor types of sensors from different manufacturers, different sensor locations on the patient's body, and different calibration procedures, among other variables.

Once the optimal hardware configuration has been identified through the DOE, it can be implemented into the remote patient monitoring system that is made available to the patient population to improve its performance and accuracy, ultimately leading to better patient outcomes, lower payer costs, and improved doctor and patient engagement.

Hardware improvements that can be implemented based on feedback provided after AI-analysis of the patient data includes upgrading the biosensors to improve the sensitivity and specificity of biomarker detection. For example, a GaN High Electron Mobility Transistor with a gold or graphene transport layer on the gate electrode can be advanced to improve the robustness, consistency and sensitivity/selectivity and limit of detection balance of the biosensor. A DOE can be constructed to improve the biosensor based on this feedback with the experiments performed during a clinical trial or tested with clinical derived patient samples, and/or with contrived samples. Also, a statistically significant sample number of MBD devices can be tested with the patient population with two or more types of biosensors included, for example, a gFET on silicon, an Au-HEMT on GaN and a printed electronic biosensor can all be included in these MBD devices and the same EBC from a patient used as the biosample that is tested by each different type of biosensor. The biomarker data obtained from these different biosensors testing the same EBC sample can be aggregated for a large number of patients using the MBD system, and the test results analyzed and compared for the different types of biosensors to determine which biosensor has the best mix of performance, cost, shelf-life, etc. This information can be used to aid in the continuous improvement of the MBD system over years of use in patient populations and over many different use-cases.

As another example of a hardware improvement, micro-fluidic channels can be modified to optimize fluid flow and sample processing, improving the accuracy and reliability of biomarker detection. For example, the microfluidic channels can be optimized with dimensions, geometry and composi-tions of a biomarker concentrating structure, such as super absorbent polymer hydrophilic channels provided on a Tef-lon hydrophilic condensate forming surface.

The Mask-Based Diagnostic (MBD) device is designed for remote patient monitoring of cardiac biomarkers using exhaled breath condensate (EBC) and biometric data using biometric sensors such as smartwatches, sensor cuffs, wraps, sleeves, patches, rings or other wearable electronics. The system includes a face mask that is worn by a patient, which collects breath vapor exhaled from the patient's lungs in a confined local environment. The MBD device also includes an EBC collector with a condensate-forming surface that converts the breath vapor into an EBC liquid sample.

The EBC testing unit of the MBD system includes a printed circuit board supporting a semiconductor packaged electronic biosensor in electrical communication with power, analysis and communications electronics. A fluid conductor conducts the EBC sample to the electronic bio-sensor. The analysis electronics detect/identify the target molecule based on an electrical signal received from the electronic biosensor, and the communications electronic components communicate the detection of the target mol-ecule. The printed circuit board includes a fluid detector onboard the printed circuit board for detecting the start and end of fluid conduction through the fluid conductor in a flow path before and after the electronic biosensor.

Many MBD devices can be deployed over a long period of time to remotely monitor a large number of patients who have had a heart attack. By collecting the EBC and biometric data from each patient on a regular basis, the system is able to identify clusters of patients with similar cardiac bio-marker patterns using an unsupervised machine learning algorithm. An artificial intelligence agent, such as Gradient Boosting Trees, is used to analyze the cardiac biomarker data from the identified clusters of patients and identify trends in the data that can be used to improve the accuracy of the MBD system for remote patient monitoring of cardiac biomarkers.

The cardiac use-case is just one example. The MBD can be configured to detect biomarkers of other diseases and health conditions, and the analysis described herein used to similarly improve the patient outcomes for a different patient population.

The MBD system provides a non-invasive, convenient, and reliable method for remote patient monitoring of cardiac biomarkers, which can significantly improve the early detec-tion of cardiovascular diseases and patient outcomes. The MBD device can be used to collect EBC biomarker data several times a day from each patient, with the time and day determined by the user interface (e.g., cellphone) or the electronics. Biometric sensors can also be used to collect biometric data such as heart rate and skin temperature. The addition of biometric data is used to improve the AI analysis and feedback by identifying second order clusters of patients with similar biomarker patterns and similar biometric pat-terns.

A medical monitoring system that uses the MBD, bio-metric sensors, a remote server, and AI algorithms can be utilized to improve patient outcomes by providing real-time and frequent monitoring and analysis of a patient's cardiac biomarker data and biometric data.

On the remote server, unsupervised machine learning algorithms are applied to the collected data to identify clusters of patients with similar cardiac biomarker patterns and similar biometric patterns. The first order clusters of patients are identified using unsupervised machine learning algorithms to analyze the cardiac biomarker data, and a principal component analysis (PCA) algorithm can then be used to analyze the data from the first order clusters of patients along with the biometric data to reduce the dimen-sionality of the data and identify a second order cluster of patients with similar cardiac biomarker patterns and similar biometric patterns.

An artificial intelligence agent, such as Gradient Boosting Trees (GBT), is configured to analyze the cardiac biomarker data from the identified second order clusters of patients and identify trends in the data that can be used to improve the accuracy of the MBD system for remote patient monitoring of cardiac biomarkers. The AI agent can provide feedback to the medical staff treating the patients, allowing them to adjust the patient's treatment plan as necessary and provide personalized care to each patient. The feedback can also be provided to the MBD manufacturer to guide improvements made to the MBD product in general and for a particular use-case. The feedback can be provided to researchers, NGO and government organizations, for example, to assist in determining where resources should be deployed, to spur new innovations and to indicate remedial steps that can be taken to lessen the impact, for example, of a pathogen on a region or population.

Gradient Boosting Trees (GBT) is a machine learning algorithm that builds a predictive model by combining an ensemble of decision trees. The algorithm is based on the principle of boosting, which is a sequential process of combining weak models to create a stronger model.

The GBT algorithm works by first creating a single decision tree, which serves as the initial model. The algo-rithm then evaluates the performance of the initial model on the collected and preprocessed patient data that can be used as training data. The algorithm identifies the instances where the model performed poorly. These instances are given higher weights, and a new decision tree is created to focus on predicting these difficult instances. This process is repeated multiple times, with each new tree focusing on the instances that were misclassified by the previous trees.

After each iteration, the algorithm adjusts the weights of the training instances based on their previous misclassifica-tion, and uses these weights to emphasize the importance of the difficult instances in subsequent trees. The algorithm continues until a stopping criterion is met, such as a maxi-mum number of trees or a minimum improvement in per-formance.

Finally, the GBT algorithm combines the predictions of all the individual trees to make a final prediction. The algorithm assigns weights to the predictions of each tree based on its performance on the training data and uses these weights to determine the final prediction.

GBT is a powerful algorithm that can handle large and complex datasets and is widely used in various applications such as classification, regression, and ranking. However, it can be prone to overfitting if the number of trees is too high or if the data is noisy. Therefore, it is important to carefully tune the hyperparameters of the algorithm to achieve the best performance.

The AI-analysis algorithms can provide various predictions based on the data obtained from the MBD system from many patients compared with the data obtained from an individual.

Prediction of patient risk: The algorithm(s) can analyze patient data and predict the likelihood of a patient developing certain conditions or diseases such as heart disease or diabetes. This can help healthcare providers to identify high-risk patients and intervene earlier to prevent or manage the disease.

Prediction of treatment outcomes: The algorithm(s) can analyze patient data and predict the effectiveness of different treatments for specific conditions. This can help healthcare providers to select the best treatment options for their patients and improve treatment outcomes.

Prediction of disease progression: The algorithm(s) can analyze patient data and predict how certain diseases may progress over time. This can help healthcare providers to anticipate changes in a patient's condition and adjust treatment plans accordingly.

Prediction of complications: The algorithm(s) can analyze patient data and predict the likelihood of a patient developing complications from a particular condition. This can help healthcare providers to identify patients who may require more intensive monitoring or treatment to prevent complications.

Pre- or post-processing of data can be used to improve the accuracy of AI-assisted predictions and feedback. For example, Principal Component Analysis (PCA) is a technique used for dimensionality reduction, where a large number of variables are simplified into a smaller number of principal components that explain most of the variation in the data. In the context of the MBD system, PCA can be used as a preprocessing step on the aggregated data obtained from many patients to identify the most important features or variables that contribute the most to the variation in the data.

The preprocessed data obtained from PCA can then be used as input for example, for a Gradient Boosting Trees (GBT) algorithm to identify trends in the data that can be used to improve patient outcomes. GBT is a machine learning algorithm that can handle both categorical and continuous data and is particularly well-suited to handle large datasets with many features. The algorithm works by iteratively adding decision trees to a model, with each subsequent tree learning from the errors of the previous tree, until the desired level of accuracy is achieved.

Due to the prevalence of cardiac disease, including heart attack and heart failure, it is likely that over time there will be a very large amount of patient data contributed and aggregated in accordance with the use of the MBD system for cardiac patients world-wide.

By using PCA as a preprocessing step on the aggregated MBD data, the dimensionality of the data can be significantly reduced, making it easier for the GBT algorithm to identify patterns and trends in the data. This can ultimately lead to improved patient outcomes by allowing healthcare professionals to make more informed decisions based on the insights obtained from the MBD system.

The system can be used to monitor patients remotely, allowing for early detection of potential cardiac events and reducing the need for re-hospitalization. By comparing an individual patient's data with the analyzed data from a large number of similarly situated patients, the system can be used to identify patients who are at higher risk for a negative impact caused by cardiovascular disease and provide targeted interventions and preventative care such as more frequent monitoring, longer hospital stays, longer duration monitoring at home, and more frequent doctor visits. The net result is a trend towards optimization of the healthcare system used by the remotely monitored patient population, which can then guide the optimization of healthcare systems in other regions and throughout the world.

FIG. 2 is a flowchart showing the steps for using the MBD utilizing AI algorithms to provide feedback that can be implemented to improve patient outcomes and to improve the MBD system.

Step 1—Collect biomarker and biometric data: Patients can use the MBD device to collect biomarker data, and biometric sensors to collect biometric data at home as frequently as needed. This data is sent to the remote server for analysis.

Step 2—Analyze biomarker data to identify first-order cluster: The remote server applies unsupervised learning algorithms to the biomarker data to identify clusters of patients with similar biomarker patterns. The server analyzes the data to identify a first-order cluster of patients.

Step 3—Analyze biometric data for patients in first-order cluster: The biometric data from patients in the first-order cluster is analyzed to identify similar biometric patterns.

Step 4—Identify second-order cluster based on similar biomarker and biometric patterns: The server applies algorithms to the first-order cluster and the biometric data analysis to identify a second-order cluster of patients with both similar biomarker patterns and similar biometric patterns.

Step 5—Analyze second-order cluster for trends in data: The data from the second-order cluster is analyzed for trends to help identify factors that may contribute to a higher likelihood of future cardiac events and/or successful recovery.

Step 6—Provide feedback for improved patient outcomes specifically for patients in the clusters and for patients that use the MBD: Based on the analysis of the second-order cluster and comparing the data obtained from an individual patient, personalized alerts can be provided to the patient or healthcare provider to take early intervention measures to improve patient outcomes. For example, the thresholds for determining a concerning condition for a particular patient can be automatically or manually adjusted based the comparison of the patient's data with AI-analyzed historical data from similarly situation patients.

Step 7—Implement changes to the MBD system based or patient treatments depending on the feedback. The changes that are implemented can include automatic adjustments to applied pharmaceutical or electroceutical treatments, changes to the user-interface, hardware and/or software utilized by the MBD system.

Different patient clusters can be obtained based on a variety of patient demographics and healthcare system factors to aid in optimizing the MBD for a particular use-case and a particular patient that fits in an identified patient cluster.

This flowchart exemplifies a system that collects biomarker and biometric data from a large number of similarly situated cardiac patients and applies AI algorithms to identify clusters of patients with similar patterns in order to provide personalized feedback to improve patient outcomes and to provide feedback to improve the MBD system for patients in a particular cluster and as overall system improvements for all or a majority of patients that use the MBD system. The use of AI algorithms such as unsupervised learning and principal component analysis allows for a more comprehensive analysis of the data to identify trends and patterns that may not be easily recognizable through traditional methods. By providing personalized alerts based on the analysis of the data, healthcare providers and patients can take proactive measures to mitigate the risk of possible future cardiac events.

In block 202, a. chemical cardiac biomarker data and non-chemical cardiac biometric data is collected from a plurality of patients using a Mask-Based Diagnostic (MBD) device and at least one biometric sensor (e.g., a wearable electronic blood pressure cuff). In block 204, b. the biomarker and biometric data are wirelessly transmitted from each patient to a gateway device, such as the patient's cellphone, doctor's office or hospital desktop computer, etc., to a remote server on the internet. In block 206, c. the biomarker and biometric data are aggregated from the plurality of patients and an unsupervised machine learning algorithm is applied to identify clusters of patients with similar cardiac biomarker and biometric patterns. In block 208, d. the data from the identified clusters of patients is analyzed using an artificial intelligence (AI) agent, such as a Recurrent Neural Network (RNN), to predict, for example, the likelihood of future cardiac events for individual patients, to provide an automatic change to the user-interface of the patients in the cluster, or (if patient identifying information is available) to alert a caregiver to a particular concerning attribute of the caregiver's patient that is a member of the particular cluster.

In block 210, e. personalized alerts can be provided to the patient, or their healthcare provider(s) based on the predicted likelihood of future cardiac events, for early intervention and improved patient outcomes. In block 212, f. the identified clusters of patients can be analyzed using a PCA algorithm to identify a second order of clusters of patients with both similar biomarker and biometric patterns. In block 214, g. the second-order cluster of patients is analyzed for trends in the data that can be used to improve the accuracy and sensitivity of the MBD system for remote patient monitoring of cardiovascular disease. In block 216, h. the feedback is implemented to improve the MBD system. In block 218, an applied treatment to the patients is adjusted based on the detected changes in the biomarker and biometric data and evaluating the effectiveness of the treatment using an AI algorithm.

Note that one or more steps of the flow chart can be obviated, or the order of the steps changed, depending on the use-case, patient population and the desired or available utilization of AI-agents to analyze the collected data to improve patient outcomes.

The MBD system utilizes the steps in the flowchart to improve patient outcomes by collecting chemical cardiac biomarker data and non-chemical cardiac biometric data from a large number of patients using an MBD and at least one biometric sensor. The collected data from each patient is transmitted to a remote server on the internet for analysis using unsupervised machine learning algorithms. The algorithms analyze the chemical biomarker data to identify clusters of patients with similar cardiac biomarker patterns and identifies a first-order cluster of patients with similar cardiac biomarker patterns. The non-chemical cardiac biometric data for each patient in the first-order cluster is then analyzed to identify a smaller second-order cluster of patients with both similar biomarker and biometric patterns.

A principal component analysis (PCA) algorithm can be applied to the data from the second-order cluster of patients to reduce the dimensionality of the data. This helps to identify trends in the data that can be used to improve the accuracy and sensitivity of the MBD system for remote patient monitoring of cardiovascular disease. Feedback based on the analyzed data is then provided to improve patient outcomes, and the feedback is implemented to improve the MBD system.

Principal component analysis (PCA) is a statistical technique used to reduce the dimensionality of a large data set while retaining as much information as possible. In the context of the MBD system, PCA can be used to analyze the biomarker and biometric data from the identified clusters of patients to identify trends in the data that can be used to improve the accuracy and sensitivity of the MBD system for remote patient monitoring of cardiovascular disease.

PCA works by identifying the underlying structure in the data and transforming the data into a new set of variables called principal components. Each principal component is a linear combination of the original variables, and the first principal component explains the most variation in the data. Subsequent principal components explain decreasing amounts of variation, and the number of principal components is determined by the user.

PCA can be used to identify patterns and correlations in the data that may not be immediately apparent from the raw data. This can be useful for identifying clusters of patients with similar biomarker and biometric patterns, as well as identifying trends in the data that can be used to improve the MBD system for remote patient monitoring of cardiovascular disease.

Alternative algorithms that can be used instead of PCA include t-SNE (t-Distributed Stochastic Neighbor Embedding), UMAP (Uniform Manifold Approximation and Projection), and LLE (Locally Linear Embedding). These algorithms are also used for dimensionality reduction and can be effective in identifying patterns and correlations in high-dimensional data sets. The choice of algorithm depends on the specific application and the nature of the data being analyzed.

In addition, an artificial intelligence (AI) agent, such as a Recurrent Neural Network (RNN), can be trained to analyze the biomarker data and predict the likelihood of future cardiac events for the individual patient. This AI agent is also used to analyze the PCA-reduced data to identify trends in the data that can be used to further improve the accuracy and sensitivity of the MBD system for remote patient monitoring of cardiovascular disease.

A Recurrent Neural Network (RNN) is a type of artificial neural network (ANN) that is particularly useful for processing sequential data such as time-series data. In the context of the MBD system, the RNN can be trained to analyze patterns in the cardiac biomarker data collected from patients using the MBD and to predict the likelihood of future cardiac events for individual patients.

The RNN works by processing a sequence of inputs (in this case, the time-series data for each patient's cardiac biomarker measurements) and using its internal state to maintain a Memory of previous inputs. This enables the RNN to learn patterns and relationships within the sequential data.

To use the RNN in the MBD system, the algorithm is first trained on a large dataset of cardiac biomarker data from a variety of patients with different medical histories, ages, genders, and other demographic factors. The algorithm then learns to recognize patterns within the data that are predictive of future cardiac events.

Once the RNN has been trained, it can be applied to new data from individual patients using the MBD. The RNN processes the time-series data for the patient's cardiac biomarker measurements and produces a prediction of the likelihood of future cardiac events for that patient. This prediction can then be used to provide personalized alerts to the patient or their healthcare provider(s), enabling early intervention and potentially improving patient outcomes.

Alternative algorithms that can be used instead of the RNN for predicting future cardiac events include Decision Trees (DT), Random Forests (RF), and Support Vector Machines (SVM). These algorithms can also be trained on large datasets of cardiac biomarker data and used to identify patterns and relationships within the data that are predictive of future cardiac events. However, they may have different strengths and weaknesses compared to the RNN and may require different training procedures or input data preprocessing steps.

For example, GBT is a machine learning algorithm that belongs to the family of decision tree-based algorithms. It works by constructing a sequence of decision trees that improve the accuracy of the predictions. In contrast, RNN is a type of neural network that is specifically designed for processing sequential data, such as time series or natural language. While both GBT and RNN are used for prediction tasks, they have different architectures and learning mechanisms. The selection of which AI algorithm to use will depend on the use-case, obtained data and other decisions. As the use of the MBD system with AI-assisted analyses progresses, comparisons of the results obtained by various algorithms in various orders of data analysis can be used to further improve the MBD remote patient monitoring system for a particular use-case, patient population or for overall general improvements.

The MBD system can also be used in conjunction with an applied treatment, such as medication or lifestyle changes, and the MBD and biosensors can detect changes to the patient's condition based on chemical biomarkers and non-chemical biometrics. The AI algorithms can then analyze the detected changes to the patient's condition and adjust the applied treatment accordingly, in real-time, to improve patient outcomes.

For example, for patients who may be susceptible to deep vein thrombosis (DVT), the MBD or other sensor can be used to monitor a biomarker called d-dimer in the patient's blood. An electroceutical treatment can be applied to the DVT patient to cause involuntary muscle contractions in the calf muscles and discharge stagnant blood through the deep veins.

As an exemplary scenario, a patient has been diagnosed with DVT and is undergoing an electroceutical treatment to help with blood flow through the deep veins. The MBD or other biosensor is being used to monitor the patient's d-dimer levels, which are an indicator of blood clot formation.

Initially, the electroceutical treatment is being applied at a constant level, and the MBD system is recording the patient's d-dimer levels over time. As the treatment continues, the AI algorithms analyzing the data from the MBD system detect an increase in the patient's d-dimer levels, indicating that blood clot formation is occurring despite the treatment.

Based on this information, the AI algorithms can automatically adjust the electroceutical treatment, either by increasing the frequency or intensity of the treatment, to prevent the blood clots from forming. The MBD system continues to monitor the patient's d-dimer levels, and the AI algorithms adjust the treatment in real-time based on the changes detected in the patient's condition.

By using the MBD system and AI algorithms in this way, healthcare providers can provide more personalized and effective treatment for DVT patients, with the potential to improve patient outcomes and reduce the risk of complications. Note that the AI-algorithms can be imbedded in the software provided with an electroceutical medical device and/or provided through a wireless link to the medical device to a remote server.

The MBD system can utilize a combination of chemical biomarker data, non-chemical biometric data, and AI algorithms to identify patient clusters with similar biomarker and biometric patterns, reduce the dimensionality of the data, identify trends in the data, and provide feedback to improve the accuracy and sensitivity of the MBD system for remote patient monitoring of a particular disease, thereby improving patient outcomes.

The method may also include further collecting treatment data from the patient, where the treatment data includes information about the applied treatment, and analyzing the treatment data along with the chemical biomarker data and non-chemical biometric data using the AI agent to identify correlations between the applied treatment and patient outcomes, and using the identified correlations to adjust the applied treatment for improved patient outcomes. Other technical features may be readily apparent to one skilled in the art from the drawing figures, descriptions, and claims.

Examples of how correlations between the applied treatment and the detected biomarker and biometrics data can be used to improve patient outcomes include:

Personalized treatment plans: By analyzing the biomarker and biometrics data alongside the applied treatment, the AI agent can identify correlations between certain treatments and specific changes in the patient's biomarker and biometric readings. This information can be used to develop personalized treatment plans that are tailored to each patient's individual needs, resulting in better outcomes.

Early intervention: If the AI agent detects that a patient's biomarker and biometric readings are indicating a potential issue, such as a risk of future cardiac events, the patient's healthcare provider can be alerted early on. This early intervention can lead to faster treatment and better outcomes for the patient.

Treatment optimization: By continuously analyzing the biomarker and biometric data alongside the applied treatment, the AI agent can identify correlations between specific treatments and their effectiveness for certain patients. This information can be used to optimize treatment plans and improve outcomes for future patients with similar biomarker and biometric profiles.

In one aspect, a mask-based diagnostic (MBD) system provides test results using an exhaled breath condensate (EBC) biosample in less than 10 minutes. The MBD 300 comprises a speaker 302, an EBC collector 304, a face mask 306, analysis electronics 308, and a biosensor 310. The EBC collector converts exhaled breath vapor into a collected liquid biosample; a biosensor generates an output signal dependent on the detection of a target biomarker in the liquid biosample; and analysis electronics 308 determine a test result from the output signal. In an accessibility version as shown, a microcontroller controls the generation of audible spoken word messages for providing automatic readout of at least one of test instructions, test progress and the test results. The EBC testing unit tests the EBC sample for the presence of the target molecule and includes the electronics provided on a printed circuit board supporting the biosensor. The biosensor is provided as a packaged semiconductor electronic biosensor in electrical communication with power, analysis and communications electronics.

Another version of the MBD with accessibility features includes communications electronics 404 for wirelessly communicating with a smartphone 406, where the speaker 402 of the smart phone is used for playing the audible spoken word messages to the user for providing automatic readout of the test instructions, progress and results. Depending on the use-case and a particular patient's needs, the accessibility features can be obviated or modified. For example, for a clinical use-case where the MBD is used to test a patient for EBC biomarkers, a skilled medical technician may administer the test with the test results being wirelessly transmitted to a local area computer or server, or directly through a local gateway to a remote internet server.

Figures 5, 6, 7:
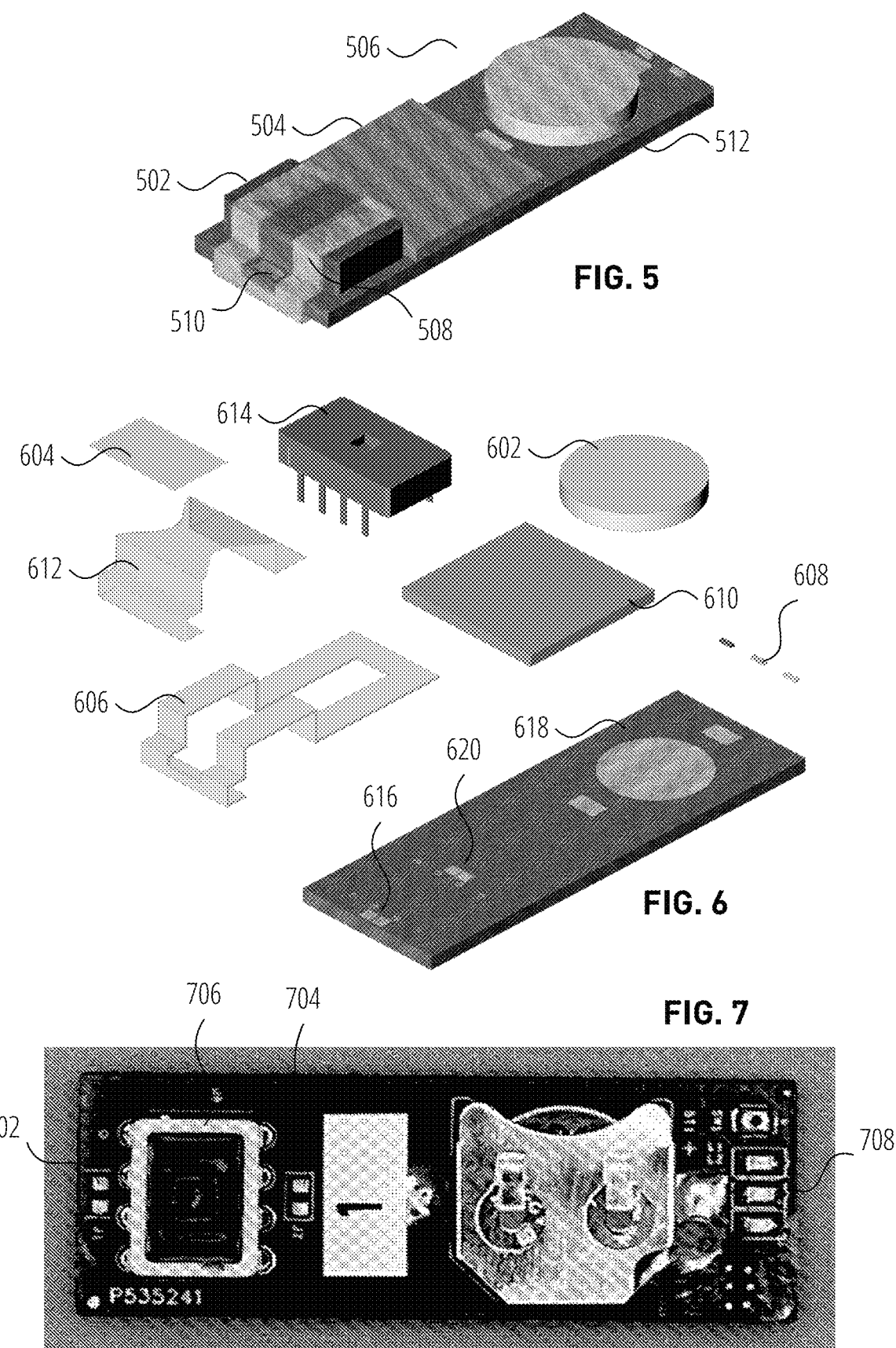
FIG. 5 illustrates an assembled EBC testing unit.
FIG. 6 is an exploded view showing components of an EBC testing unit.
FIG. 7 illustrates a printed circuit board having a biosensor, fluid detectors, analysis and communications electronics and a battery.

FIG. 5 illustrates an assembled EBC testing unit. The EBC testing unit includes the biosensor 502, the EBC testing unit 506, a wick 504, a fluid conductor 508, a fluid detector 510, and a printed circuit board 512. The fluid conductor conducts the EBC sample to the electronic biosensor. The mask-based diagnostic device may also include the electronics and biosensor as components of an EBC testing unit for testing the liquid sample for the target biomarker, where the EBC sample contains water and the target molecule, along with relatively low levels of test confounding molecules and ions. The EBC testing unit includes the electronics formed on a printed circuit board supporting the biosensor provided as a semiconductor packaged electronic biosensor in electrical communication with power, analysis and communications electronics. A fluid conductor, such as microfluidic channels comprising a suitable material is provided for conducting the EBC sample to the electronic biosensor. The mask-based diagnostic device may also include the electronics and biosensor as components of an EBC testing unit for testing the liquid sample for the target biomarker.

FIG. 6 is an exploded view showing components of an EBC testing unit 204. The EBC testing unit includes the biosensor 502, the wick 504, the fluid conductor 508, the fluid detector 510, the printed circuit board 512, a battery 602, a light emitting diode LED 608, a microfluidic cover 604, and a microfluidic adhesive 606. The fluid detectors 510 onboard the printed circuit board detects when EBC is flowing through the fluid conductor and into the detection well of the biosensor. As an example, the fluid detector comprises a pair of parallel conductors on the printed circuit board with a gap of about 0.02" between the conductors that enables the detection of the presence of EBC in the section of the fluid conductor in contact with the parallel conductors. When EBC is present, an electrical signal can flow from one of the parallel conductors through the EBC to the other parallel conductor to complete an electrical circuit and indicate the EBC flow. Two or more sets of fluid detectors can be provided on the printed circuit board. Either or both the start of fluid conduction through the fluid conductor in a flow path before the electronic biosensor and the end of fluid conduction in the flow path after the electronic biosensor can be detected by the respective fluid detectors. The EBC testing unit also includes the printed circuit board supporting the semiconductor packaged electronic biosensor in electrical communication with power, analysis and communications electronics. The detection of EBC flow can be used to automatically start the process for testing the EBC sample and transmitting the obtained data to the patient's cellphone and/or to the remote server.

In addition, or alternatively, a physical switch can be provided on the printed circuit board to initiate the testing, and/or a smartphone or computer user-interface wirelessly connected with the microcontroller or microprocessor onboard the PCB can be used to control the test. Also, the detection of the EBC at the second fluid detector (in the EBC flow path after the biosensor) can be used to indicate if the test is invalid, for example, if the EBC flow does not reach the second fluid detector.

The printed circuit board of an embodiment the MBD device comprises a fluid detector 702, a fluid detector 704, a biosensor 706, and an LED 708. The printed circuit board can be provided as a component that is integrated into or supported on the face mask, or provided as a table-top unit where and EBC sample is collected from the MBD (e.g., using a pipette) and deposited into a detection well of the biosensor.

Figure 8:
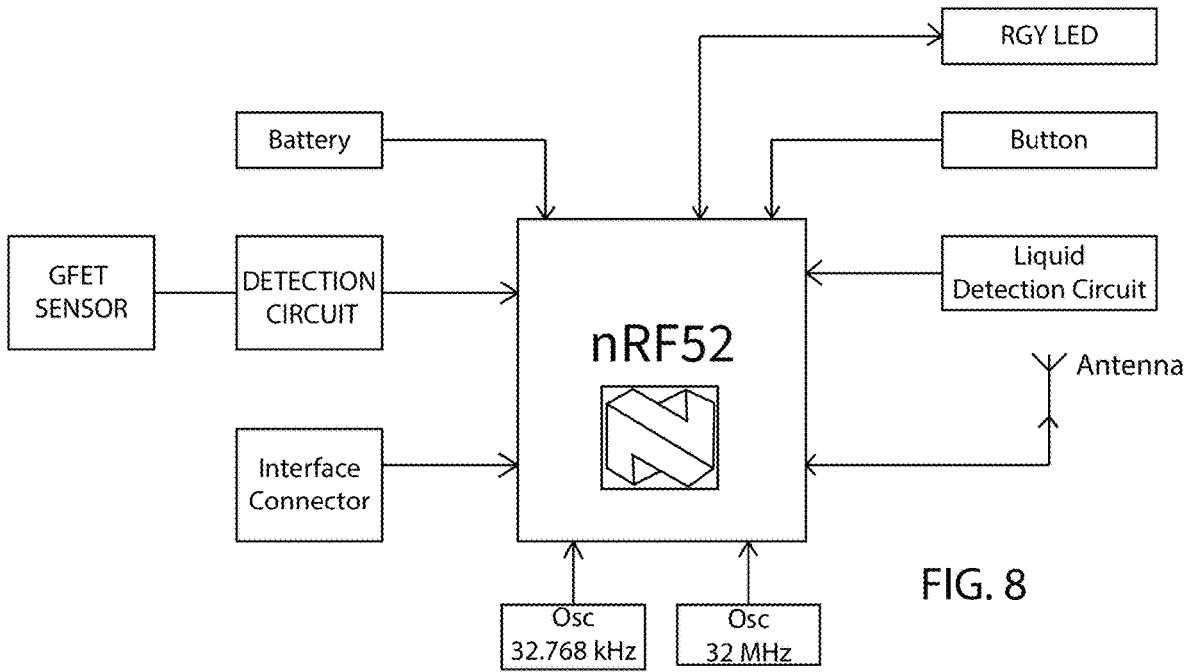
FIG. 8 is a schematic of the EBC testing unit with Bluetooth communication capability.

FIG. 8 is a block diagram of the electronic circuit of an EBC test unit. The EBC test unit includes a biosensor 202, a fluid detector 306, a battery 402, analysis electronics 502, communications electronics 506, and one or more test result/progress indicating LEDs 606 may also be provided (for example, to provide a self-contained testing system that can be used by a hearing-impaired individual). The analysis electronics detect the target molecule dependent on an electrical signal received from the electronic biosensor. The various components can be incorporated as elements on the printed circuit board or as components of a system-on-chip package which may also include the biosensor. The communications electronics communicates the detection of the target molecule to a user through an indicator, such as a light emitting diode or smartphone, computer or tablet display. The communications electronics can communicate the detection of the target molecule wirelessly through an optical or radio frequency (RF) signal, for example, Bluetooth communication to a smart phone or network relay device.

A valid test can be determined depending on if the fluid detectors detect the fluid conduction of the liquid sample past the biosensor. Once a valid test has been determined, the test results can be automatically transmitted for AI-assisted analysis as described herein.

FIG. 9 illustrates a routine 900 for improving the accuracy of the MBD system for remote patient monitoring of cardiac biomarkers, in accordance with one embodiment. In block 902, routine 900 collects cardiac biomarker data from a plurality of patients using MBD devices and transmits the data wirelessly from the MBD to a relay device, such as a cellphone, local area gateway device, or other relay, and transmits the data to a remote server on the internet. In block 904, routine 900 aggregates the cardiac biomarker data from the plurality of patients and identifies clusters of patients with similar cardiac biomarker patterns using an unsupervised machine learning algorithm. In block 906, routine 900 analyzes the cardiac biomarker data from the identified clusters of patients using an artificial intelligence agent, such as GBT, to identify trends in the data. In block 908, routine 900 uses the identified trends in the data to develop feedback to suggest specific tangible improvements to the MBD system that can be implemented for remote patient monitoring of cardiac biomarkers.

Some tangible improvements that can be determined from an aggregated large dataset of biomarker data obtained from a large population of similarly situated patients using the MBD to test each patient's EBC for the same biomarker include: Identification of the most reliable biomarker(s) for remote patient monitoring of cardiac biomarkers; Development of more accurate reference ranges for different biomarkers that can be used for early detection and diagnosis of cardiac diseases; Identification of the specific biomarker(s) that correlate with certain types of cardiac diseases or conditions; and Development of personalized treatment plans based on a patient's individual biomarker profile.

An AI-agent can use the identified trends in the data to develop feedback to suggest specific tangible improvements to the MBD system for remote patient monitoring of cardiac biomarkers in several ways, such as: Recommending changes to the MBD system's hardware or software to improve accuracy and reliability of the biomarker data; Developing more sophisticated algorithms for data analysis that can detect patterns and correlations in the biomarker data that are not immediately apparent to human analysts; Recommending changes to the testing protocol that can improve the consistency and quality of the EBC samples collected by patients using the MBD system; and Identifying potential risks or issues with the MBD system and suggesting strategies to mitigate them.

Overall, an AI-agent can use the insights gained from the analysis of large datasets of biomarker data to suggest specific improvements to the MBD system that can improve the quality of care for patients with cardiac diseases.

This flowchart describes a method for improving the accuracy of the MBD system for remote patient monitoring of cardiac biomarkers. The first step involves collecting cardiac biomarker data from a plurality of patients using MBD devices and transmitting the data wirelessly to a server on the internet.

The second step involves aggregating the cardiac biomarker data from the plurality of patients and identifying clusters of patients with similar cardiac biomarker patterns using an unsupervised machine learning algorithm. This step helps to group patients with similar biomarker patterns, allowing for more targeted analysis and feedback.

The third step involves analyzing the cardiac biomarker data from the identified clusters of patients using an artificial intelligence agent, such as GBT, to identify trends in the data. This step helps to identify patterns and correlations between different biomarkers, as well as patient demographics and other factors that may affect their cardiac health.

Finally, the identified trends in the data are used to develop and implement improvements to the MBD system for remote patient monitoring of cardiac biomarkers. These improvements may include modifications to the MBD device or its sensors, as well as changes to the AI algorithms or the way in which data is collected and analyzed. Overall, this method provides a more personalized approach to patient monitoring, leading to improved accuracy in predicting and preventing future cardiac events.

GBT stands for Gradient Boosted Trees, which is a type of machine learning algorithm that can be used for classification and regression tasks. GBT works by building an ensemble of decision trees, where each subsequent decision tree corrects the errors of the previous one. Other types of machine learning and artificial intelligence algorithms can also be used utilized in this exemplary embodiment to help improve the MBD system and provide better patient outcomes.

In the context of the MBD system for remote patient monitoring of cardiac biomarkers, GBT can be used as an artificial intelligence agent to analyze the cardiac biomarker data from identified clusters of patients and identify trends in the data. These trends can then be used to develop and implement improvements to the MBD system to improve its accuracy in remote patient monitoring of cardiac biomarkers.

GBT can be used to perform feature selection, where it identifies which biomarkers are most important in predicting future cardiac events. This information can then be used to improve the design of the MBD by optimizing the selection and number of biosensors used to detect specific biomarkers.

GBT can also be used to develop predictive models, where it uses the identified trends in the data to predict the likelihood of future cardiac events for individual patients. This information can then be used to provide personalized alerts to patients or their healthcare providers for early intervention and improved patient outcomes.

In block 1002, a) cardiac biomarker data is collected from a patient using a Mask-Based Diagnostic (MBD) device and the data transmitted wirelessly from the MBD or table-top reader to a gateway device, such as a cellphone, router or relay, and then to a server on the internet. In block 1004, b) the cardiac biomarker data is analyzed using an artificial intelligence (AI) agent to identify trends in the data and predict the likelihood of future cardiac events for the individual patient. In block 1006, c) as an example of a tangible utilization of the AI analyzed data, personalized alerts can be provided by the MBD system (e.g., through a cellphone user interface) to the patient or (e.g., through a desktop computer dashboard) to the patient's healthcare provider based on the predicted likelihood of future cardiac events, for treatment modification, early intervention and other proactive, manual and/or automatic efforts and that result in improved patient outcomes.

The MBD is a non-invasive diagnostic device that can collect exhaled breath condensate (EBC) and detect cardiac biomarkers using multiplexed biosensors and synthetic bioreceptors. As a use-case example, the MBD is used to collect chemical cardiac biomarker data from a large number of patients with cardiovascular disease. This data is then wirelessly transmitted to a remote server on the internet.

The server is configured to receive and aggregate the cardiac biomarker data from the plurality of MBD devices and apply an unsupervised machine learning algorithm to identify clusters of patients with similar cardiac biomarker patterns. The identified clusters of patients are then analyzed using an artificial intelligence agent, such as a recurrent neural network (RNN), to predict the likelihood of future cardiac events for each individual patient.

The system also includes a smartphone APP that is in communication with the MBD device. The APP can be configured to receive and analyze the biomarker data generated by the MBD device, on its own or in conjunction with a remote server. The APP uses the RNN predictions to provide personalized alerts to the patient or their healthcare provider based on the predicted likelihood of future cardiac events. The alerts provide early intervention and improved patient outcomes.

The RNN algorithm is a type of artificial neural network that is particularly useful for processing sequential data, such as the time-series data obtained from the MBD in this system. The RNN is trained using historical data (e.g., from one particular patient and/or from an aggregation of data from similarly situated patients) to identify patterns and relationships in the data, which it can then use to make predictions about future events.

For example, the RNN can trained using historical bio-marker data obtained from the MBD, along with information about the patient's medical history, lifestyle factors, and other relevant information. The RNN analyzes the data to identify patterns and relationships that are indicative of increased risk of future cardiac events, such as changes in certain biomarkers over time or correlations between bio-markers and lifestyle factors.

For example, the RNN may identify a pattern of increas-ing levels of a specific biomarker over time, which is associated with an increased risk of future cardiac events. Or the RNN may identify a correlation between a patient's biomarker levels and their exercise habits, which can be used to identify patients who are at increased risk due to a lack of physical activity.

Once the RNN has analyzed the data and identified patterns and relationships, it can use this information to make predictions about the likelihood of future cardiac events for each patient. These predictions can then be used to provide personalized alerts and interventions for patients who are at increased risk, allowing for earlier diagnosis and treatment and improved patient outcomes.

FIG. 11 shows a patient wearing an MBD 1102 for obtaining chemical biomarker test data from EBC and a wrist cuff wearable electronic 1106 that can include a suite of biometric sensors 1104 for obtaining non-chemical bio-metric data of measurable physiological metric such as blood pressure, heart rate, heart rate variability, skin tem-perature, blood oxygen levels, blood flow, etc.

In an MBD system that collects cardiac biomarker data, such as troponin and NT-proBNP, and non-chemical cardiac biometric data, such as EKG and blood pressure, an AI-agent can be used to provide feedback to suggest improve-ments to the system. The feedback can be based on the analysis of all or a portion of the aggregated data, including the biomarker and biometric data, as well as de-identified demographic data, time of day of testing for each biomarker and biometric, and time since the patient had a heart attack.

The AI-agent can utilize machine learning algorithms to identify patterns and trends in the data, such as correlations between biomarker levels and biometric data, or how the time of day of testing or time since the patient had a heart attack affects the biomarker or biometric readings. This analysis can help to identify areas where the MBD system can be improved, such as by adjusting the frequency of testing for certain biomarkers or biometrics, or by refining the thresholds used to determine when a patient is at risk for a cardiac event.

For example, the AI-agent may identify that patients who have a high level of troponin and low blood pressure in the morning are at higher risk for a cardiac event. Based on this insight, the MBD system could be programmed to test these patients more frequently or to alert their healthcare provider if their biomarker and biometric readings reach, exceed or drop below a certain threshold.

In addition to identifying patterns and trends in the data, the AI-agent can also use predictive analytics to forecast future outcomes for patients based on their biomarker and biometric data. For example, the AI-agent may predict that a patient is at increased risk for a cardiac event in the near future based on their biomarker and biometric readings and additional patient data. This information can be used to develop more personalized treatment plans or to provide patients with targeted interventions to reduce their risk.

The use of an AI-agent to analyze the biomarker and biometric data collected by the MBD system can help to improve the accuracy and utility of the system for remote patient monitoring of cardiovascular disease. By providing feedback and suggestions for improvement based on the analysis of all the aggregated data, the MBD system can be continually refined and updated to better serve the needs of patients and healthcare providers.

One example of a type of wireless EKG system that could be used with the MBD is the AliveCor KardiaMobile device. This device is a small, portable EKG monitor that can be attached to a smartphone to record EKG readings. The device uses Bluetooth to wirelessly transmit the EKG data to the smartphone, where it can be analyzed and shared with healthcare providers. The device also includes AI-powered algorithms to provide real-time analysis of the EKG data and detect any anomalies. The KardiaMobile device can be used by patients at home and is FDA-cleared for medical use.

One example of a type of wireless blood pressure moni-toring system that can be used with the MBD is the Omron Evolv Bluetooth Wireless Upper Arm Blood Pressure Moni-tor. This device connects wirelessly to a smartphone or tablet and allows for easy and convenient blood pressure moni-toring at home. The device has a compact design and uses Bluetooth technology to transmit data to the user's smart-phone or tablet, which can then be uploaded to a server for analysis. The Omron Evolv is also equipped with advanced features such as multi-user support, automatic averaging of the last three readings, and the ability to detect irregular heartbeats during measurement.

In accordance with an exemplary embodiment, the bio-metric data obtained from these biometric sensors with wireless readout can be collected by an APP of the MBD system and the data logged and formatted for transmission to the remote server as part of the patient data associated with the particular patient.

Other biometrics that could be useful for a cardiac patient that uses the MBD include: Oxygen saturation (SpO2): This measures the amount of oxygen in a patient's blood and can be useful in monitoring the effectiveness of treatments such as oxygen therapy or the efficacy of a body system, such as the heart and lungs; Heart rate variability (HRV): This measures the variation in time between heartbeats and can be used to assess the health of the autonomic nervous system, which regulates heart rate and other involuntary body functions; Respiration rate: This measures the number of breaths a patient takes per minute and can be useful in monitoring patients with respiratory symptoms of conditions such as heart failure; Body temperature: This measures a patient's body temperature and can be useful in monitoring patients with infections or other conditions that can affect body temperature and cardiac performance; Activity level: This measures a patient's level of physical activity and can be useful in monitoring patients with heart disease or other conditions that affect mobility and/or that benefit from cardiovascular exercise. At least some of these biometric sensors will be useful for other diseases that are remotely monitored using the MBD and the choice of biometric data collected depends on the specific needs of the patient and the goals of the MBD system. For example, for Covid-19 at-home monitoring, the MBD used along with blood oxy-gen and temperature biometric sensing could allow patients to stay home and reduce the chances of infecting others, while still enable the monitoring of important biometrics indicating how the disease is progressing and whether they potentially require hospital or doctor's office intervention.

The additional patient data, such as de-identified demographic data, time of day of testing for each biomarker and biometric, time since a heart attack, can be utilized by the AI-agent to identify potential correlations and trends in the data. For example, the AI-agent can analyze the biomarker and biometric data collected from patients who had a heart attack within the past week and compare it to the data collected from patients who had a heart attack more than a week ago. The AI-agent can then identify any differences or similarities in the data and use this information to suggest improvements to the MBD system.

In addition, the AI-agent can analyze the biomarker and biometric data based on the patients' demographics such as age, sex, and ethnicity. This can help identify any differences in the data based on demographic factors and suggest improvements that take these factors into account.

The time of day of testing for each biomarker and biometric can also be utilized by the AI-agent to identify any patterns or trends in the data. For example, if there is a consistent trend of higher troponin levels in the morning, the AI-agent can suggest that patients be advised to take their MBD tests at a consistent time of day to minimize variability in the data. The additional patient data can provide valuable context for the AI-agent to analyze the biomarker and biometric data and suggest improvements to the MBD system that take into account the unique characteristics of each patient.

FIG. 12 is flow chart of a method for improving the accuracy of an MBD system for remote patient monitoring of cardiovascular disease by analyzing both chemical cardiac biomarker data and non-chemical cardiac biometric data. The flow chart starts with the collection of data from a large number of patients and proceeds through a series of steps that includes identifying clusters of patients with similar biomarker patterns, identifying a smaller cluster of patients with both similar biomarker and biometric patterns, applying PCA to reduce the dimensionality of the data, and analyzing the reduced data to identify trends that can be used to improve the MBD system. Feedback is provided to improve patient outcomes, and the feedback is implemented to improve the MBD system. The method utilizes AI analysis of data collected from patients to identify patterns and trends in the data, which can be used to develop more targeted interventions and personalized treatment plans. PCA is applied to the data to simplify complex datasets and focus on the most relevant variables, leading to a more precise and accurate analysis of the data and improved patient outcomes.

In block 1202, chemical cardiac biomarker data and non-chemical cardiac biometric data are collected from a large number of patients using an MBD device to collect the biomarker data and at least one biometric sensor to collect the biometric data. In block 1204, the chemical cardiac biomarker data is analyzed by an AI agent to identify clusters of patients with similar cardiac biomarker patterns. In block 1206, a first order cluster of patients is identified by the AI agent, the first order cluster is a cluster of patients with similar cardiac biomarker patterns. In block 1208, the AI agent analyzes non-chemical cardiac biometric data for each patient in the first order cluster to identify a smaller second order cluster of patients with both similar biomarker and biometric patterns. In block 1210, the AI agent applies a principal component analysis (PCA) algorithm to the data from the second order cluster of patients to reduce the dimensionality of the data. In block 1212, the AI agent analyses the PCA-reduced data to identify trends in the data that can be used to improve the accuracy of the MBD system for remote patient monitoring of cardiovascular disease. In block 1214, the AI agent provides feedback based on the analyzed data to improve patient outcomes. In block 1216, this feedback from the AI agent is implemented to improve the MBD system.

This flow chart describes a method for improving the accuracy of an MBD system for remote patient monitoring of cardiovascular disease by analyzing both chemical cardiac biomarker data and non-chemical cardiac biometric data. The flow chart starts with the collection of data from a large number of patients and proceeds through a series of steps that includes identifying clusters of patients with similar biomarker patterns, identifying a smaller cluster of patients with both similar biomarker and biometric patterns, applying PCA to reduce the dimensionality of the data, and analyzing the reduced data to identify trends that can be used to improve the MBD system. Feedback is provided to improve patient outcomes, and the feedback is implemented to improve the MBD system.

This flow chart is an example of a method utilizing AI analysis of data collected from patients for improving the accuracy and utility of the MBD system for remote patient monitoring of cardiovascular disease. In this example, patient generated data comes from the use of the MBD to obtain cardiac biomarker data from a cardiac patient along with biometric data from biometrics sensors, such as wearable electronic devices worn by the same patient.

For example, by using unsupervised analysis of both chemical cardiac biomarker data and non-chemical cardiac biometric data from a large number of patients, patterns or trends can be determined for biomarker and biometric data so that a defined group of patients with similar disease progression and recovery characteristics are determined or identified from measured objective data (biomarker and biosensor).

Besides PCA, there are several other algorithms that could be used to improve the analysis of the collected biomarker and biometric data:

Independent Component Analysis (ICA): Similar to PCA, ICA is a statistical technique used to reduce the dimensionality of large datasets. However, ICA is able to identify underlying independent sources in the data, whereas PCA identifies underlying patterns and correlations.

Random Forests: Random forests is a machine learning algorithm that can be used for classification or regression tasks. It works by constructing a multitude of decision trees at training time and outputting the class that is the mode of the classes (classification) or mean prediction (regression) of the individual trees.

Support Vector Machines (SVMs): SVMs are a type of supervised machine learning algorithm that can be used for classification or regression tasks. They work by finding the hyperplane that best separates the data into different classes.

Neural Networks: Neural networks are a family of machine learning algorithms inspired by the structure and function of the human brain. They can be used for classification or regression tasks and are particularly useful for processing complex, nonlinear data.

The choice of algorithm will depend on the specific characteristics of the data and the analysis task at hand. A combination of different algorithms may be used to achieve the best results.

In the specific cardiac use-case example, the MBD system can collect cardiac biomarker data, such as troponin and NT-proBNP, and non-chemical cardiac biometric data, such as EKG and blood pressure from a large number of cardiac patients who have had a recent heart attack. An AI-agent can be used to provide feedback to suggest improvements to the system. The feedback can be based on the analysis of all the aggregated data, including the biomarker and biometric data, as well as de-identified demographic data, time of day of testing for each biomarker and biometric, and time since the patient had a heart attack.

The AI-agent can utilize machine learning algorithms to identify patterns and trends in the data, such as correlations between biomarker levels and biometric data, or how the time of day of testing or time since the patient had a heart attack affects the biomarker or biometric readings. This analysis can help to identify areas where the MBD system can be improved, such as by adjusting the frequency of testing for certain biomarkers or biometrics, or by refining the thresholds used to determine when a patient is at risk for a cardiac event.

In addition to identifying patterns and trends in the data, the AI-agent can also use predictive analytics to forecast future outcomes for patients based on their biomarker and biometric data. For example, the AI-agent may predict that a patient is at increased risk for another cardiac event in the near future based on their biomarker and biometric readings and additional patient data. This information can be used to develop more personalized treatment plans or to provide patients with timely and targeted interventions to reduce their risk.

The additional patient data, such as de-identified demographic data, time of day of testing for each biomarker and biometric, time since they had a heart attack, can be utilized by the AI-agent to identify potential correlations and trends in the data. For example, the AI-agent can analyze the biomarker and biometric data collected from patients who had a heart attack within the past week and compare it to the data collected from patients who had a heart attack more than a week ago. The AI-agent can then identify any differences or similarities in the data and use this information to suggest improvements to the MBD system.

The additional patient data can provide valuable context for the AI-agent to analyze the biomarker and biometric data and suggest improvements to the MBD system that take into account the unique characteristics of each patient. The number of successive clusters, order of data analysis and identification of clusters of patients can be altered and compared to identify new patterns and trends. For example, the additional patient data can be analyzed first to cluster patients into a first order cluster, then the biometric data used to identify the second order cluster, then the biomarker data used to identify the third order cluster, and the results compared with a different third order cluster obtained by a different order of data analysis.

Some examples of chemical biomarkers for MBD detected cardiac biomarkers include: a) Troponin: Troponin is a cardiac biomarker that is used to detect damage to the heart muscle. It can be measured using a chemical assay, such as a troponin I or troponin T test; b) NT-proBNP: NT-proBNP is a cardiac biomarker that is used to diagnose heart failure. It can be measured using a chemical assay, such as an NT-proBNP test; c) CRP: CRP is a biomarker of inflammation that can be used to predict the risk of cardiovascular disease. It can be measured using a chemical assay, such as a high-sensitivity CRP test; d) Lipid profile: Lipid profile is a group of biomarkers that can be used to assess the risk of cardiovascular disease. It includes total cholesterol, HDL cholesterol, LDL cholesterol, and triglycerides. At least some of the lipid profile biomarkers, e.g., lipid peroxidation products (LPPs) can be tested for from an EBC sample, others can be measured using a chemical assay, such as a lipid panel test. Other biomarkers that may relate to heart disease or another concerning medical condition include products of nitrogen oxide metabolism, hydrogen ions, hydrogen peroxide, cytokines, proteins, and DNA.

The MBD system can use a combination of wearable electronic biometric sensors and EBC tested biomarkers to collect chemical cardiac biomarker data and non-chemical cardiac biometric data from a plurality of patients. The collected data can be transmitted wirelessly to a server on the internet and aggregated for analysis. An unsupervised machine learning algorithm can be applied to identify clusters of patients with similar cardiac biomarker and biometric patterns. The identified clusters of patients can be analyzed using an AI agent, such as a recurrent neural network (RNN), to predict the likelihood of future cardiac events for individual patients. Personalized alerts can be provided to the patient, or their healthcare provider, based on the predicted likelihood of imminent or future cardiac events, for early intervention and improved patient outcomes. The identified clusters of patients can also be analyzed using a PCA algorithm to identify a second order of clusters of patients with both similar biomarker and biometric patterns. The second-order clusters of patients can be analyzed for trends in the data that can be used to improve the accuracy and sensitivity of the MBD system for remote patient monitoring of cardiovascular disease. The feedback can be implemented to improve the MBD system, and an applied treatment can be applied to the patients based on the detected changes in the biomarker and biometric data. The effectiveness of the treatment can be evaluated using an AI algorithm.

FIG. 13 is a flow chart showing the use of collected patient data accumulated along with chemical biomarker and non-chemical biosensor data. In block 1302, routine 1300 collects cardiac biomarker data and non-chemical cardiac biometric data from individual patients using a plurality of MBD devices and biometric sensors, respectively. In block 1304, routine 1300 transmits the data wirelessly to a server on the internet. In block 1306, routine 1300 collects patient data including at least one of demographic information, time and date of onset of a concerning cardiac condition, physical activity of the patient, family history of cardiac disease, age of patient, occupation of patient and sex of patient. In block 1308, routine 1300 transmits the data wirelessly to the server on the internet. In block 1310, routine 1300 aggregates the cardiac biomarker data, non-chemical cardiac biometric data, and patient data from the plurality of MBD devices, biometric sensors, and patient data sources on the server. In block 1312, routine 1300 analyzes the aggregated data using an unsupervised machine learning algorithm to identify clusters of patients with similar cardiac biomarker patterns, similar non-chemical cardiac biometric patterns, and similar patient data. In block 1314, routine 1300 providing feedback dependent on the biomarker, biometric and patient data. In block 1316, routine 1300 implements improvements to at least one hardware, software and network component depending on the provided feedback.

Figure 14:
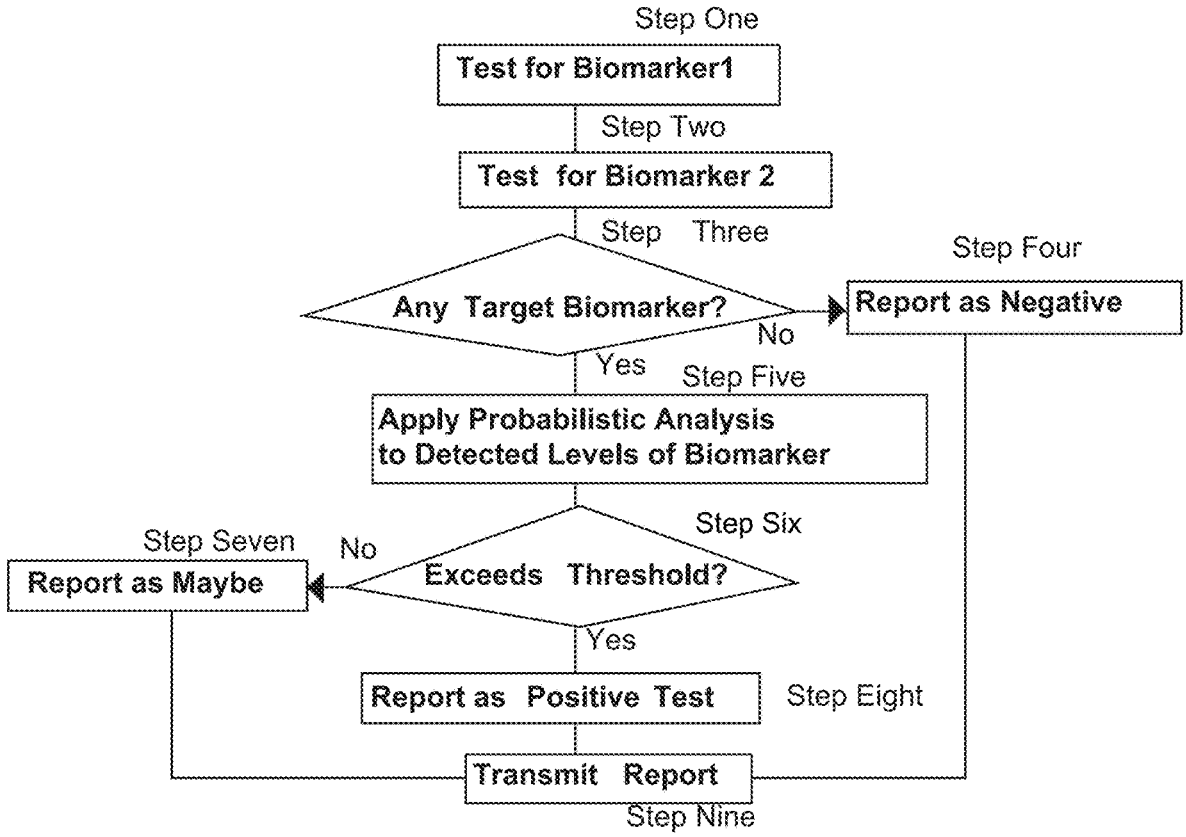
FIG. 14 is a logic flow diagram for Applied Probabilistic Analysis to determine the detecting of a target biomarker, and illustrates the operation of an exemplary method utilized by an exemplary diagnostic device and electronic medical records database.

FIG. 14 is a logic flow diagram for Applied Probabilistic Analysis to determine the detection of a target biomarker, and illustrates the operation of an exemplary method, a result of execution of computer program instructions embodied on a computer readable Memory, functions performed by logic implemented in hardware, and/or interconnected means for performing functions in accordance with exemplary embodiments.

As an example of a use-case for diagnosing and monitoring a pathogen infection, such as Covid-19, applied probabilistic analysis can be used to improve the predictive model of an individual's infection status and in the aggregate, help to refine the testing results thresholds for an objective quantitative or qualitative testing system. In accordance with an exemplary embodiment, a method is provided for the applied probabilistic analysis to the test results for two or more biomarkers to determine pathogen exposure. Host-generated biomarkers resulting from the immune response of the patient can be combined with virus biomarkers such N- or S-proteins of the SARS-CoV-2 virus. In accordance with this example, Biomarker1 is first tested for (step one), Biomarker2 is then tested for (step two). Additionally, BiomarkerN is tested for where N can be any number of multiple biomarkers tested using the inventive testing system. If no target biomarker is detected (step three) then a Negative Test report is generated (step four). If any target biomarker is detected (step three) then probabilistic analysis may be performed depending simply on the detected presence (yes/no) or quantitative analysis (e.g., concentration) of the one or more detected biomarkers (step five). The probabilistic analysis can be performed using an updated probability model where probabilistic multipliers for the tested-for biomarkers are determined for a population. As an example, if a virus outbreak occurs earlier in time in a region or country different from the location of the currently applied testing, the probabilistic multipliers for the tested-for biomarkers can be determined from confirmed cases occurring during the earlier outbreak. A threshold can be determined for the results of the probabilistic analysis based on the probabilistic multipliers obtained from the confirmed cases and help to improve the accuracy of the testing system. As an example, in an electronic biosensor, a threshold voltage for considering a test result as positive can be adjusted based on the probabilistic analysis of previously tested and confirmed positive cases. Over time, the accuracy and confidence of positive and negative determinations is improved based on the history of confirmed cases and obtained threshold voltages. As the database of tested cases grows, the overall testing regimen with interconnected communication, sharing and analysis of tests results is used to automatically improve the accuracy and confidence of future tests.

If the probabilistic analysis does not exceed a threshold (step six) (e.g., low concentration of a particular target biomarker, or the presence of just one weak biomarker indicating likely infection), then a Maybe Test report is generated (step seven). The ability to detect a possible infection that isn't necessarily confirmed positive could be important during an early stage of a new pandemic or regional outbreak since it is important to identify possible infections and remove the possibly infected individuals from unnecessary contact with other until their infection status can be confirm. If the probabilistic analysis does exceed a threshold (step six) (e.g., high concentration of a particular target biomarker, or the presence of two or more biomarkers indicating likely infection), then a Positive Test report is generated (step eight). The Test Report is then transmitted (step nine) (e.g., in a manner described herein or other suitable transmission mechanism including verbal, digital, written or other communication transmission that adds to the accumulated database of test results).

The logic flow is implemented by a non-limiting embodiment of an apparatus, comprising at least one Processor; and at least one Memory including computer program code, the at least one Memory and the computer program code configured to, with the at least one Processor, cause the apparatus to perform at least the following: detecting one or more biometric parameters using a droplet harvesting structure for converting breath vapor to a fluid droplet for forming a fluid sample and a testing system having a biomarker testing zone for receiving the fluid sample and detecting the biometric parameter, where the biometric parameters are biomarkers dependent on at least one physiological change to a patient in response to a concerning condition such as a virus infection; receiving the one or more biometric parameters and applying probabilistic analysis to determine if at least one physiological change threshold has been exceeded dependent on the probabilistic analysis of the one or more biometric parameters; and activating an action depending on the determined exceeded said at least one physiological change.

In accordance with an embodiment, a biosensor testing device is provided having one or more biometric detectors each for detecting biomarkers as one or more biometric parameters. The biometric parameters are dependent on at least one physiological change to a patient or test subject, such as the production of immune response chemicals, the presence in the body of an active or deactivated virus or virus component, antibodies, antigens, virus RNA, or other biomarker inducing change (including an immune response or viral load count). A microprocessor receives the one or more biometric parameters and determines if at least one physiological change threshold has been exceeded depending on the one or more biometric parameters. An activation circuit activates an action depending on the determined physiological change. The action includes at least one of transmitting an alert, modifying a therapeutic treatment, and transmitting data dependent on at least one physiological change, the one or more biometric parameters, and therapeutic treatment.

The inventive mask-based diagnostic platform, and/or components of the platform described herein, can also be used to monitor the progression of a disease in a patient, for example, a hospitalized patient that is going through the disease progression of Covid-19. The at least one physiological change can also be in response to an applied therapeutic treatment that causes a change in the condition of the patient to enable the monitoring of the body's response to an applied therapeutic. The action can include transmitting an alert, modifying a therapeutic treatment, and transmitting data dependent on at least one of the at least one physiological change, the one or more biometric parameters, and therapeutic treatment. The microprocessor can analyze the one or more biometric parameters using probabilistic analysis comprising determining from a data set of the one or more biometric parameters whether the data set is acceptable for deciding that the at least one physiological change threshold has been exceeded. The probabilistic analysis can further comprise applying a statistical weighting to each of the one or more biometric parameters, where the statistical weighting is dependent on a predetermined value of a ranking of importance in detecting each of the at least one physiological change for said each of the one or more biometric parameters relative to others of the one or more biometric parameters.

The MDB system can utilize the logic flow diagram for Applied Probabilistic Analysis in conjunction with an AI-agent that can perform the analysis of the collected biomarker data. The AI-agent can be designed to analyze the aggregated data from the remote server to identify patterns and trends in the data, and determine if a threshold has been exceeded for the at least one physiological change. The AI-agent can also determine if any target biomarker has been detected and perform the probabilistic analysis using an updated probability model.

In addition, the AI-agent can apply a statistical weighting to each of the biometric parameters, which can help to determine the ranking of importance in detecting each of the at least one physiological change for said each of the one or more biometric parameters relative to others of the one or more biometric parameters. This can further help to improve the accuracy and confidence of positive and negative determinations.

The AI-agent can provide feedback based on the identified patterns and trends in the data and the results of the probabilistic analysis. This feedback can be used to improve the efficacy of the remote patient monitoring system by implementing the feedback to optimize at least one hardware, software, and networking component of the remote patient monitoring system.

There are several AI algorithms that can be utilized to automate the analysis of collected biomarker data in accordance with the Applied Probabilistic Analysis process described by the flowchart. One such algorithm is the Bayesian network, which is a probabilistic graphical model that represents a set of variables and their conditional dependencies using a directed acyclic graph. Bayesian networks can be used to model the probability distribution over the biomarkers and other variables, allowing for the calculation of conditional probabilities and the updating of the probability distribution as new data is collected. Other AI algorithms that can be used for biomarker data analysis include support vector machines (SVMs), random forests, and deep learning neural networks.

Figure 15:
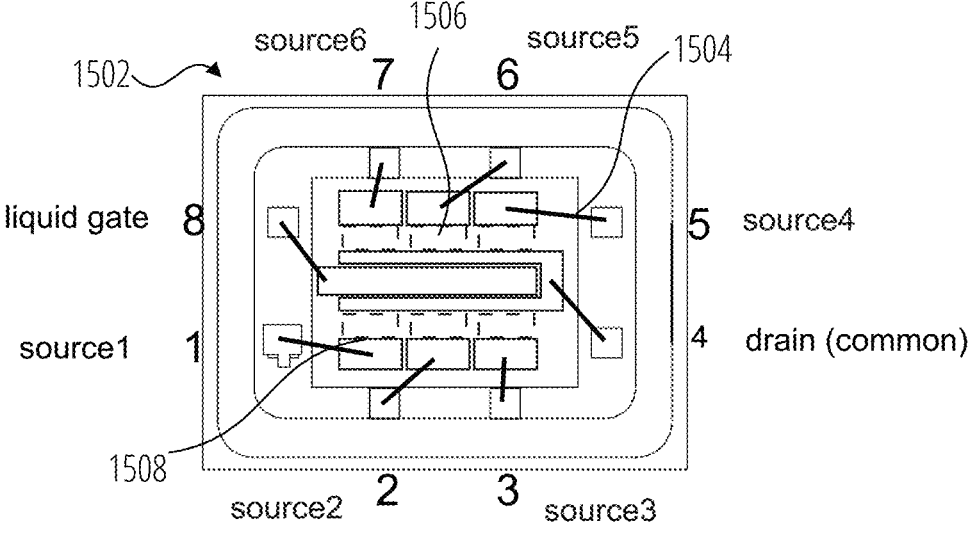
FIG. 15 illustrates a single bare die wire bonded for semiconductor packaging and having multiple and differently functionalized g-FET biosensors.

FIG. 15 illustrates a single bare die wire bonded for semiconductor packaging and having multiple and differently functionalized gFET biosensors. The charge transfer layer 1506 of each gFET 1508 on the bare die semiconductor device is functionalized with a different set of capture molecules. A DIP package 1502 is constructed using conventional semiconductor electronic circuit device materials and processes including wire bonds 1504 connecting the electrodes of the gFET biosensor features (sources, drains, liquid gate) to respective pins of the DIP package. An encapsulation process encases the bare die and leaves an opening so that the detection areas of the gFETs are accessible to the sample being tested.

Figure 16:
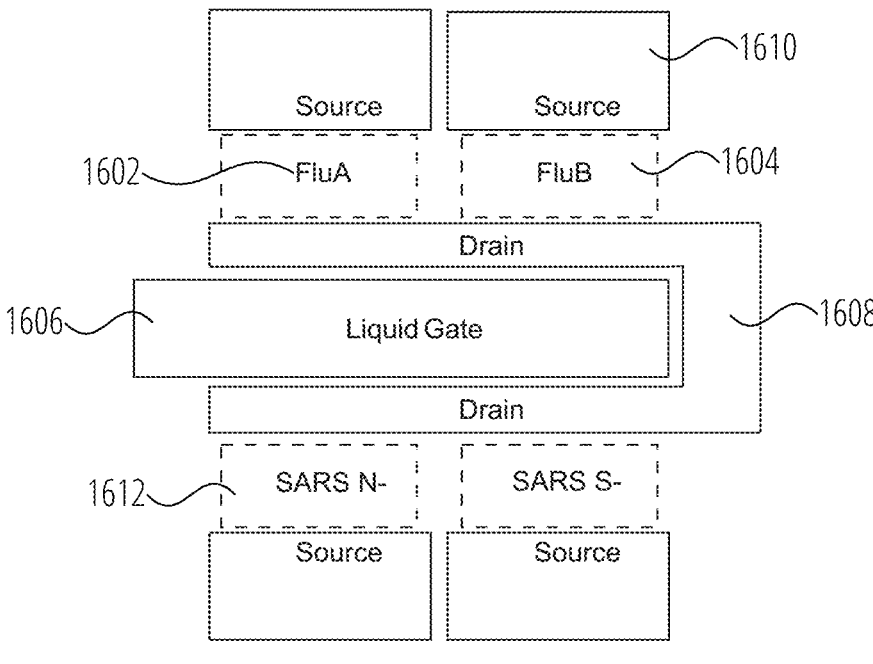
FIG. 16 illustrates bare die biosensor having g-FET devices functionalized for FluA/FluB/SARS virus testing.

FIG. 16 illustrates a bare die biosensor having ggFET devices functionalized for FluA/FluB/SARS virus testing. In this case, each gFET on the bare die semiconductor device is functionalized for detecting if the test sample contains a biomarker of FluA, FluB or SARS. In this example, the biosensor consists of a gFET semiconductor device, however other semiconductor structures, such as an Au—GaN biosensor could be utilized, or printed electronic, electrochemical, LFAs, or other biosensors could be utilized by the MBD.

In this example, the SARS biomarkers include both the SARS N-protein and S-protein. Each charge transfer layer 1506 of the different gFETs has a different type of capture molecule (e.g., capture molecule1 1602 for detecting FluA biomarker). The capture molecules are immobilized at the detection area 1604 of each corresponding gFET. A liquid gate electrode 1606, a drain electrode 1608, and a source electrode 1610 provide electrical conduction to the semiconductor features that form the different biosensors ganged on semiconductor bare die, where one or more of these biosensors can be functionalized at the processed wafer level.

The present invention is designed as a modular system of subassemblies, each module can be separately completed and tested to ensure their functionality before being integrated into the MBD system. This modular approach facilitates rapid reconfiguration of the MBD system to respond to new pathogen threats, new disease use-cases and rapid implementation of improvements developed by engineers with AI-assisted improvement guidance. The packaged biosensor can have multiple gFET sensors on a single bare die, and each sensor can be individually functionalized with a different capture molecule. This allows for the creation of a syndromic biosensor that can test for multiple biomarkers of the same disease (e.g., S and N proteins and even RNA of SARS-CoV-2 virus) and/or different diseases (e.g., SARS, Flu-A, Flu-B).

As an exemplary use-case for pathogen monitoring, the MBD system utilizing AI agents can be useful in detecting variants of COVID-19 causing virus. The MBD system can be used to collect samples of exhaled breath condensate (EBC) from individuals infected with COVID-19, and these samples can be analyzed using multiplexed biosensors and synthetic bioreceptors to detect specific biomarkers associated with the virus. The MBD system could be used to collect non-chemical biometric data from these individuals, which could be analyzed along with the biomarker data to identify specific patterns of biometric data in a given population associated with COVID-19 infection.

AI agents, such as neural networks, can be trained to analyze these patterns of data and identify specific biomarkers and biometric patterns associated with different variants of the COVID-19 virus. This can allow healthcare professionals to quickly and accurately identify patients infected with these variants, and to develop targeted treatment and prevention strategies.

Furthermore, the MBD system can also be used to track the spread of these variants over time, by collecting and analyzing data from a large number of patients. The AI agents can be trained to identify specific patterns of biomarker and biometric data associated with different geographical regions or populations, and to track the movement of these variants over time. This allows healthcare professionals to quickly identify new outbreaks of these variants and to implement targeted interventions to control their spread.

Referring to FIG. 17, block 1702, routine 1700 (a) collecting exhaled breath condensate (EBC) samples from individuals using a Mask-Based Diagnostic (MBD) device, wherein the MBD device is configured to detect a panel of biomarkers includes respective biomarkers of FluA, FluB, SARS S-protein, and SARS N-protein. In block 1704, routine 1700 (b) transmits the collected EBC samples to a server for analysis and storage. In block 1706, routine 1700 (c) applies an unsupervised machine learning algorithm to the aggregated EBC data to identify clusters of patients with similar biomarker patterns. In block 1708, routine 1700 (d) uses an artificial intelligence (AI) agent, such as a Recurrent Neural Network (RNN), trained on the biomarker panel data, to analyze the identified clusters of patients and detect new variants of respiratory infections. In block 1710, routine 1700 (e) applies a prediction model to the data generated by the AI agent to predict the spread of the new variants to other regions based on the location and travel history of the patients in the identified clusters. In block 1712, routine 1700 (f) providing personalized alerts to at least one of healthcare providers and public health authorities based on the predicted spread of the new variants for early intervention and improved public health outcomes.

The MBD system can be configured to detect multiple biomarkers in EBC, including the S-protein and N-protein of the SARS virus. As mentioned, the N-protein of the SARS virus does not mutate and remains stable in the population, while the S-protein mutates and causes variants of the SARS-CoV-2 virus to appear in the population of infected people.

To detect a new variant of SARS-CoV-2 occurring in a region, the MBD system can be used to collect EBC samples from individuals in the region and analyze the samples using a panel test that includes the S-protein biomarker. The MBD system can then transmit the biomarker data wirelessly to a server on the internet, where an AI agent, such as a recurrent neural network (RNN), can be trained to detect and identify patterns in the S-protein biomarker data.

The AI agent can be trained using machine learning algorithms, including unsupervised clustering and supervised classification algorithms, to detect patterns in the S-protein biomarker data that are indicative of the presence of a new variant of SARS-CoV-2. For example, if the N-protein is detected in most patients that test positive for SARS-CoV-2 infection, but for some patients the S-protein is not detected or weakly detected, this could indicate a new mutation of the virus that escapes detection by the currently used S-protein capture molecules immobilized on the biosensor. These patterns could include changes in the levels of the S-protein biomarker that are distinct from the levels observed in previous variants of the virus, indicating that there is the possibility of the presence of a new variant in the tested population.

Once the AI agent has detected a potential new variant of SARS-CoV-2, the system can provide alerts to healthcare providers and public health officials, allowing for early detection and response to the emergence of a new variant. This early detection can help to limit the spread of the variant and inform efforts to develop targeted treatments and vaccines. The MBD system utilizing AI agents has the potential to play a valuable role in detecting and tracking emerging variants of SARS-CoV-2, helping to inform public health efforts to control the pandemic. Provisions can be made to contact individuals that are suspected to be infected with a new variant and further testing can be performed to confirm if a new variant is present in the population.

The MBD system utilizing AI agents could be used to predict the spread of the new variant of SARS-CoV-2 from one region to another by analyzing the patterns of transmission of the virus, using the data collected from the MBD devices and other sources, such as social media, travel data, and epidemiological models.

The MBD devices can be used to monitor the prevalence of the new variant in the region where it first appeared. The AI agent can analyze the data collected from the MBD devices to identify the biomarker patterns associated with the new variant and compare them to those of an earlier strain. This can help in identifying the spread of the new variant and estimating its transmission rate.

The AI agent can use access to smartphone data to analyze the travel data of infected individuals to predict the movement of the new variant from one region to another. By analyzing the travel patterns of infected individuals, the AI agent can predict the likelihood of the new variant spreading to other regions, as well as the rate at which it is likely to spread. This can be used to predict the potential impact of the new variant on the global spread of the virus. As a privacy precaution, access to the smartphone data can be voluntary and requested only when a variant is determined infecting a particular patient, and the obtained smartphone data can be automatically stripped of specific patient identifying data before it is transmitted to the internet server.

The AI agent can use epidemiological models to predict the spread of the new variant, for example, based on previous virus spread in a population or region. The AI agent can analyze the data collected from the MBD devices and other sources, such as hospital admission rates, mortality rates, and vaccination rates, to build models that can predict the future trajectory of the new variant. These models can be used to estimate the potential impact of the new variant on public health, and to inform public health policy decisions.

The MBD system utilizing AI agents can be a powerful tool for predicting the spread of a new variant of SARS-CoV-2, or the entry of a new pathogen into the population in a given state, country or region, and the transmission from one region to another. By analyzing patterns of transmission, travel data, and epidemiological models, the system can provide early warnings of potential outbreaks, and help to inform public health policy decisions.

The present invention can be used as a remote patient monitoring (RPM) system, which allows healthcare providers to monitor patients outside of a clinical setting. RPM is likely to become an essential tool to proactively assess patients' health and enable timely intervention before an adverse event occurs. The MBD diagnostic platform includes the electronics for Bluetooth communication and encryption of data obtained as a direct-to-electrical signal generated by the gFET biosensor. Encrypted test results can be relayed from a smartphone through the internet to trusted receivers and public authorities. The test results can be automatically wirelessly transmitted and displayed in minutes from putting the mask on and breathing normally.

The MBD can be configured for testing different biomarkers found in EBC that are relevant to a particular disease or as a panel test to help diagnose a particular disease from among a variety of diseases that are consistent with patient symptoms, demographics, biological or environmental exposures, etc., other potential pandemic diseases, such as tuberculosis.

For monitoring diabetes patients, an MBD system can be configured to detect glucose and hbA1c biomarkers, and other diabetes related biomarkers, in EBC using the aforementioned gFET nanosensor or a AlGaN/GaN HEMT. The MBD device can collect patient data in real-time and transmit the data to a remote server where it can be analyzed by an AI agent to identify patterns and trends in the data. Feedback can then be generated based on the identified patterns and trends, which can be used to improve the efficacy of the remote patient monitoring system. The data collected can also be aggregated with that of other diabetes patients using the MBD to provide insights for healthcare professionals and government agencies to improve the outcomes of the patient population.

The advantage of using the MBD system for glucose monitoring is that it is non-invasive, unlike current blood glucose detection methods that can be painful and invasive. This can encourage patients to monitor their glucose levels more frequently, which can improve their glycemic control and ultimately lead to better patient outcomes. The MBD system with AI-assistance can also provide personalized feedback to patients based on their individual data, which can help them make more informed decisions about their diabetes management. Additionally, the aggregated data from multiple patients can provide insights for healthcare professionals and government agencies to develop more effective diabetes management strategies.

GaN HEMTs (high electron mobility transistors) are particularly useful for diabetes biomarker monitoring using the MBD due to their sensitivity, stability, and reproducibility. The HEMT can be immobilized with glucose oxidase, which catalyzes the oxidation of glucose to produce hydrogen peroxide. This hydrogen peroxide can then be detected by the HEMT, which produces a corresponding electrical signal. The sensitivity of the HEMT allows for detection of glucose concentrations ranging from 0.5 nM to 125 μM, making it suitable for monitoring glucose levels in diabetic patients. In addition, the HEMT's high stability and reproducibility make it an ideal choice for continuous monitoring of glucose levels over extended periods of time, such as with the MBD device. The wireless capabilities of the MBD device can allow for real-time monitoring and feedback to both patients and healthcare professionals, allowing for timely intervention and improved patient outcomes. The data collected from the MBD devices can also be aggregated and analyzed to provide insights into larger trends and patterns in diabetes biomarker levels, which can inform public health initiatives and improve the care of the diabetes patient population as a whole.

The MBD system can utilize AI agents for drug discovery by analyzing the chemical cardiac biomarker data collected from the patients using the MBD and identifying potential drug targets. The AI agents can use machine learning algorithms to identify correlations between the biomarker data and specific genes, proteins, or pathways involved in a particular disease, such as cardiovascular disease.

Once potential drug targets are identified, AI agents can be used to screen vast libraries of compounds to identify those with the desired properties. The AI agents can use techniques such as virtual screening, molecular docking, and machine learning-based approaches to identify compounds that are predicted to bind to the target and have desirable pharmacological properties.

Furthermore, the MBD system can be utilized in clinical trials for new drugs, where AI agents can be used to analyze biomarker data from the trial participants and identify those who respond well to the treatment. This can allow for more personalized medicine and the development of drugs that are tailored to specific patient populations.

The MBD system can utilize AI agents for drug discovery by analyzing biomarker data, identifying potential drug targets, screening compounds, and optimizing clinical trials. This approach has the potential to accelerate drug discovery and improve patient outcomes by enabling the development of more effective and personalized treatments for cardiovascular disease.

The MBD system can utilize AI agents for population studies in several ways. First, the system can collect biomarker data from a large and diverse population using the MBD devices and biometric sensors, which can be analyzed to identify trends and patterns in the data. AI algorithms such as unsupervised learning, clustering, and association rule mining can be used to identify relationships between biomarkers and other health factors, such as demographics, lifestyle, and environmental factors.

This analysis can provide valuable insights into the underlying causes of a specific disease and inform public health policies and interventions. For example, if certain demographic groups are found to have a higher risk of developing heart disease, targeted prevention and intervention programs can be developed to address these disparities. Similarly, if certain environmental factors are found to be associated with higher rates of cardiovascular disease, policies can be developed to mitigate these factors.

Another way the MBD system can utilize AI agents for population studies is by using the collected data to develop predictive models for a particular disease. These models can be used to identify individuals who are at high risk for developing heart disease and to guide targeted prevention and intervention efforts. Machine learning algorithms such as logistic regression, decision trees, and random forests can be used to develop these models, which can incorporate a variety of factors such as biomarker data, biometric data, demographic information, and medical history.

In addition, the MBD system can be used to monitor the effectiveness of interventions and treatments on a population level. By collecting biomarker data and biometric data before and after treatment, the system can provide insights into the effectiveness of different treatment strategies and inform clinical decision-making. AI algorithms such as natural language processing and sentiment analysis can also be used to analyze patient feedback and improve patient satisfaction and adherence to treatment plans.

The MBD system can be utilized in population studies of other diseases by collecting chemical biomarker data found in EBC and non-chemical biometric data from wearable electronic biometric sensor from a large number of patients with the disease of interest. The collected data can then be analyzed using unsupervised machine learning algorithms to identify clusters of patients with similar biomarker and biometric patterns.

Once these clusters have been identified, AI agents can be used to analyze the data to identify trends and patterns that may be indicative of the disease and can be used to improve diagnosis and treatment. For example, in a study of respiratory diseases, such as asthma or chronic obstructive pulmonary disease (COPD), the MBD system can be used to collect exhaled breath condensate (EBC) and detect biomarkers associated with the disease. The biometric sensors can be used to collect additional data such as heart rate and respiratory rate.

Unsupervised machine learning algorithms can be used to identify clusters of patients with similar biomarker and biometric patterns, and AI agents such as deep learning or neural networks can be used to analyze the data and identify trends that may be indicative of the disease. The data can also be used to develop predictive models to identify patients at risk for future exacerbations or complications.

The MBD system can also be used in population studies of infectious diseases, such as COVID-19, by collecting and analyzing biomarker and non-chemical biometric data from patients. The data can be used to identify trends in disease progression, identify risk factors for severe disease, and develop predictive models to identify patients who may be at risk for severe disease or complications.

The MBD system and AI agents can be a powerful tool in population studies of various diseases, allowing for the collection and analysis of large amounts of data to improve diagnosis, treatment, and patient outcomes.

The MBD system can utilize AI agents to implement improvements by analyzing the biomarker and biometric data collected from a large number of patients using the MBD devices and biometric sensors. The AI agents, such as unsupervised machine learning algorithms and PCA algorithms, can identify patterns and trends in the data that may suggest areas of improvement for the MBD system.

For example, if the AI analysis identifies that certain cardiac biomarkers are frequently missed or inconsistently detected by the MBD devices, then improvements can be made to the biosensors or the collection method to ensure more accurate and consistent data collection. Additionally, if the analysis identifies certain biometric sensors that are less reliable or less effective in detecting relevant biometric data, then improvements can be made to the sensors or the data collection methods to ensure more reliable and accurate biometric data.

Furthermore, the AI agents can also analyze the data to identify patient populations that may benefit from more personalized or targeted monitoring and treatment, allowing for further improvement in patient outcomes. Overall, the MBD system can continuously use AI analysis to identify areas of improvement and make necessary changes to enhance the accuracy, sensitivity, and effectiveness of the system.

The MBD system can be augmented with additional data sources such as conventional clinical laboratory tests, patient demographics, patient questionnaires, doctor questionnaires, AI web crawlers, and statistical models to implement improvements to the MBD system utilizing AI agents. These additional data sources can provide a wealth of information that can be used to improve the accuracy and sensitivity of the MBD system in detecting and predicting cardiac events.

For example, patient demographics such as age, gender, and medical history can provide important context for interpreting the biomarker and biometric data collected by the MBD system. Patient questionnaires can provide additional information on lifestyle factors such as diet, exercise, and smoking that may impact cardiovascular health. Doctor questionnaires can provide insights into medical history, medication usage, and other relevant health information. AI web crawlers can collect and analyze publicly available information on environmental factors that may impact cardiovascular health such as air quality, temperature, and humidity. Statistical models can be used to integrate all of this information to predict the likelihood of future cardiac events in individual patients.

The AI agents can analyze the combined data from these various sources to identify trends and correlations that can be used to improve the accuracy and sensitivity of the MBD system. For example, the AI agents can use the additional data sources to identify patterns in biomarker and biometric data that are associated with certain environmental factors or lifestyle choices. These patterns can then be used to develop targeted interventions and treatment plans for individual patients.

In addition, the AI agents can be used to continuously monitor and analyze the data from the MBD system and other sources to identify any new patterns or trends that emerge over time. This can enable the MBD system to adapt and improve its predictive capabilities over time as new information becomes available.

Below is a code snippet that demonstrates a simple implementation of the flow chart shown in FIG. 1. This code snippet is for exemplary purposes and modifications to the code will vary depending on how data is collected, the types of AI algorithms used, type of data, etc. This example code snippet defines several functions that collect data from individual patients, transmit the data to a remote server, aggregate the data on the server, analyze the aggregated data using an AI agent, generate feedback based on the identified patterns and trends, and provide and implement the feedback to improve the remote patient monitoring system. The code uses the requests library in Python to perform HTTP requests to a remote server, and the json library to encode and decode JSON data. The actual implementation of the code will depend on the specifics of the remote patient monitoring system and the data being collected.

Example Computer Code

```
import requests import json
# Collect data from individual patients def collect_data
(patient_id): # Collect patient data here and return
as a dictionary data={'patient_id': patient_id,
'biomarker_data': biomarker_data, 'biometric_data':
biometric_data} return data
# Transmit data to remote server def transmit_data(data):
url="http://remote_server_url/data_endpoint"
headers={'Content-type': 'application/json'}
response=requests.post(url, data=json.dumps(data),
headers=headers) return response.status_code
# Aggregate data on remote server def aggregate_data( ):
url="http://remote_server_url/data_endpoint"
headers={'Content-type': 'application/json'}
response=requests.get(url, headers=headers) return
response.json( )
# Analyze aggregated data using AI agent def
analyze_data(data): # Use AI algorithms to analyze
data and identify patterns and trends
patterns=identify_patterns_and_trends(data) return
patterns
# Generate feedback based on identified patterns and
trends def generate_feedback(patterns):
feedback=generate_feedback_from_patterns(patterns)
return feedback
# Provide feedback to improve remote patient monitoring
system def provide_feedback(feedback): url="http://
remote_server_url/feedback_endpoint"
headers={'Content-type': 'application/json'}
response=requests.post(url, data=json.dumps(feed-
back), headers=headers) return response.status_code
# Implement feedback to improve remote patient moni-
toring system def implement_feedback(feedback): #
Use feedback to improve at least one hardware, soft-
ware and networking component of the remote patient
monitoring system improve_system_components(feed-
back)
# Main function to run the method def main( ): patien-
t_ids=['patient1', 'patient2', 'patient3'] # List of
patient IDs for patient_id in patient_ids:
data=collect_data(patient_id)
status_code=transmit_data(data)
aggregated_data=aggregate_data(                )
patterns=analyze_data(aggregated_data)
feedback=generate_feedback(patterns)
status_code=provide_feedback(feedback)
implement_feedback(feedback)
```

What is claimed is:

1. A method of operating a diagnostic system using exhaled breath condensate (EBC) as a biosample, the diagnostic system comprising:

(a) an EBC collector having a condensate forming surface that converts exhaled breath vapor into an EBC liquid sample, the EBC collector being cooled before use so that the condensate forming surface is at a condensation forming temperature lower than a confined environment temperature inside of the face mask, and (b) an EBC testing unit comprising (i) a biosensor configured to output an electrical signal, (ii) power, analysis and communications electronics in electrical communication with the biosensor, the analysis electronics configured to detect a target molecule dependent on the electrical signal received from the biosensor, and the communications electronics configured to communicate a detection of the target molecule, and (iii) a fluid conductor configured to conduct the EBC liquid sample to the biosensor; and the method comprising:

acquiring from an individual patient, using the biosensor, chemical biomarker data from the exhaled breath condensate (EBC) collected from the individual patient and non-chemical biometric data determined for the individual patient;

transmitting the chemical biomarker data and the non-chemical biometric data as individual patient data to a remote server;

aggregating the individual patient data with corresponding other patient data received from a set of other patients to form a first aggregated data set;

using the first aggregated data set to train a machine-learning AI agent to form a model to identify clusters having similar chemical biomarker and/or non-chemical biometric data as the individual patient and to estimate cluster-specific metrics, where the training includes (i) applying an unsupervised algorithm to the first aggregated data set to assign the individual patient to a first order patient cluster that is a subset of the set of other patients, (ii) constructing a labeled training data set from the chemical biomarker and/or non-chemical biometric data of the first order patient cluster, and (iii) applying a trained model algorithm on the labeled training data set to compute first order cluster-specific metrics for the first order patient cluster and produce trained model parameters based on the labeled training data set, generating feedback, based on the trained model parameters, the feedback provided as automatically implementable actions to improve efficacy of the diagnostic system; and providing the feedback to the diagnostic system for implementing the feedback to improve at least one hardware, software and networking component of the diagnostic system, including adjusting at least one operational parameter of the diagnostic system, the at least one operational parameter selected from the group consisting of a software setting, a hardware configuration, a network algorithm, a diagnostic threshold, a sampling frequency, a biomarker selection, and an alert routing.

2. The method of claim 1, where a software improvement of the diagnostic system operation is controlled based on the trained model parameters, where the software improvement includes automatically changing a user-interface to provide an indication to the individual patient to change at least one of a time of use and a frequency of use of at least one of a chemical biomarker testing system and a biometric detecting system used by the diagnostic system.

3. The method of claim 1, where a hardware improvement of the diagnostic system operation is automatically controlled based on the trained model parameters, where the hardware improvement includes changing a biosensor to detect a new chemical biomarker.

4. The method of claim 1, where a network improvement of the diagnostic system operation is automatically controlled based on the trained model parameters, where the network improvement includes changing algorithms to include at least one of a new AI agent, an algorithm to preprocess the individual data, the other patient data, the model to identify clusters, the unsupervised algorithm and/or the trained model algorithm.

5. The method of claim 1, further comprising aggregating a second aggregated data set comprised of the chemical biomarker and/or non-chemical biometric data from patients in the first order patient cluster, and applying the unsupervised algorithm, or another unsupervised algorithm, to the second aggregated data set; assign the individual patient to a second order patient cluster that is a subset of the first order patient cluster; constructing the labeled training data set from the chemical biomarker and/or non-chemical biometric data from patients in the second order patient cluster; and, then applying the trained model algorithm to compute second order cluster-specific metrics for the second order patient cluster to produce the trained model parameters.

6. The method of claim 5, where the individual patient data and the corresponding patient data include demographic information, and further comprising aggregating a third aggregated data set comprised of the demographic data of the second order patient cluster, constructing the labeled training data set from the demographic data and then applying the trained model algorithm to compute third order cluster-specific metrics for the third order patient cluster to produce the trained model parameters.

7. The method of claim 1, wherein training the machine-learning AI agent comprises executing a gradient-boosting procedure.

8. The method of claim 7 where the gradient-boosting procedure:

(a) initializes a decision-tree model on collected and preprocessed patient data;

(b) iteratively identifies misclassified training instances, increases their weights, and fits additional decision trees focused on those instances; and (c) combines the predictions of the decision trees with weights based on training performance to produce the trained model parameters, the foregoing being performed by at least one processor and memory of the remote server.

9. The method of claim 1, wherein training the machine-learning AI agent comprises training a recurrent neural network (RNN).

10. The method of claim 9, wherein the RNN processes sequences of patient inputs comprising EBC biomarker measurements and non-chemical biometric measurements, the RNN maintaining an internal recurrent state across sequence elements to model temporal dependencies, and optimizing network parameters to reduce prediction error with respect to the labels of the labeled training data set, the foregoing executed by at least one processor and memory of the remote server.

11. The method of claim 10, wherein running the trained recurrent neural network on the at least one processor and memory of the remote server produces at least one of (i) a calibrated diagnostic risk score for the individual patient and (ii) trained model outputs specifying a control parameter vector; and further comprising generating, based on the trained model parameters, a control signal encoding the control parameter vector, and transmitting the control signal to the diagnostic system to automatically control the diagnostic system based on the trained model parameters, the control parameter vector specifying at least one of: a diagnostic decision threshold; an EBC collection sampling frequency or schedule; a selection of a biomarker panel or biosensor; and alert routing.

12. The method of claim 1, where the biosensor comprises at least one lateral flow assay and/or electronic biosensor.

13. The method of claim 1, wherein constructing the labeled training data set comprises, for each training example drawn from the first-order patient cluster: (a) forming an input from the individual patient's EBC chemical biomarker measurements and non-chemical biometric measurements for a defined window, (b) executing an Applied Probabilistic Analysis (APA) decision logic on the input using thresholded probability model outputs to assign a test-report class selected from Positive, Negative, or Maybe, and (c) storing the input together with the assigned test-report class as the label to create a labeled training example, optionally substituting a confirmed diagnostic outcome as the label when available.

14. The method of claim 1, further comprising preprocessing the chemical biomarker data and the non-chemical biometric data to form combined input variables for the training of the machine-learning AI agent, wherein the preprocessing comprises at least one of:
    (i) time-aligning and/or resampling the biomarker and biometric measurements to a common cadence;
    (ii) normalizing measurements relative to a baseline or control and suppressing outliers; and
    (iii) performing principal component analysis (PCA) to reduce dimensionality;
    and wherein the preprocessing is performed by at least one of the diagnostic system, a gateway device, and the remote server.

15. A non-transitory computer-readable storage medium for operating a diagnostic system using exhaled breath condensate (EBC) as a biosample, the diagnostic system comprising:
    (a) an EBC collector having a condensate forming surface that converts exhaled breath vapor into an EBC liquid sample, the EBC collector being cooled before use so that the condensate forming surface is at a condensation forming temperature lower than a confined environment temperature inside of the face mask, and
    (b) an EBC testing unit comprising (i) a biosensor configured to output an electrical signal, (ii) power, analysis and communications electronics in electrical communication with the biosensor, the analysis electronics configured to detect a target molecule dependent on the electrical signal received from the biosensor, and the communications electronics configured to communicate a detection of the target molecule, and (iii) a fluid conductor configured to conduct the EBC liquid sample to the biosensor; and
    the method comprising:
        using the computer-readable storage medium including instructions that when executed by a computer, cause the computer to:
        acquire using a first wearable electronic device worn by an individual patient, from the individual patient, using a biosensor, chemical biomarker data from the exhaled breath condensate (EBC) collected from the individual patient and non-chemical biometric data determined for the individual patient by the first wearable electronic device and/or a second wearable electronic device;
        receive, at a remote server the chemical biomarker data and the non-chemical biometric data as individual patient data;
        at the remote server aggregate the individual patient data with corresponding other patient data received from a set of other patients to form a first aggregated data set; and
        using the first aggregated data set to train a machine-learning AI agent to form a model to identify clusters having similar chemical biomarker and/or non-chemical biometric data as the individual patient and to estimate cluster-specific metrics, where the training includes (i) applying an unsupervised algorithm to the first aggregated data set to assign the individual patient to a first order patient cluster that is a subset of the set of other patients,
    (ii) constructing a labeled training data set from the chemical biomarker and/or non-chemical biometric data of the first order patient cluster, and
    (iii) applying a trained model algorithm on the labeled training data set to compute first order cluster-specific metrics for the first order patient cluster and produce trained model parameters based on the labeled training data set, generating feedback, based on the trained model parameters, the feedback provided as automatically implementable actions to improve efficacy of the diagnostic system; and
    providing the feedback to the diagnostic system for implementing the feedback to improve at least one hardware, software and networking component of the diagnostic system, including adjusting at least one operational parameter of the diagnostic system, the at least one operational parameter selected from the group consisting of a software setting, a hardware configuration, a network algorithm, a diagnostic threshold, a sampling frequency, a biomarker selection, and an alert routing.

16. The non-transitory computer-readable storage medium of claim 15, where a software improvement of the diagnostic system operation is controlled based on the trained model parameters, where the software improvement includes changing a user-interface to provide an indication to the individual patient to change at least one of a time of use, a frequency of use, at least one of a chemical biomarker testing system and a non-biometrics detecting system used by the remote patient monitoring system.

17. The non-transitory computer-readable storage medium of claim 15, where a hardware improvement of the diagnostic operation is controlled based on the trained model parameters, where the hardware improvement includes changing a biosensor to detect a new chemical biomarker.

18. The non-transitory computer-readable storage medium of claim 15, where a network improvement of the diagnostic system operation is controlled based on the trained model parameters, where the network improvement includes changing algorithms running on the remote server to include at least one of a new AI agent, an algorithm to preprocess the individual data, the other patient data, the model to identify clusters, the unsupervised algorithm and/or the trained model algorithm.

19. The non-transitory computer-readable storage medium of claim 15, wherein training the machine-learning AI agent comprises at least one of training (i) a recurrent neural network (RNN), (ii) a gradient-boosted decision-tree ensemble, (iii) a decision tree, (iv) a random forest, or (v) a support vector machine.

20. A diagnostic system comprising:
    a first diagnostic system including (a) an EBC collector having a condensate forming surface that converts exhaled breath vapor into an EBC liquid sample, the EBC collector being cooled before use so that the condensate forming surface is at a condensation forming temperature lower than a confined environment temperature inside of the face mask, and
    (b) an EBC testing unit comprising (i) a biosensor configured to output an electrical signal, (ii) power, analysis and communications electronics in electrical communication with the biosensor, the analysis electronics configured to detect a target molecule dependent on the electrical signal received from the biosensor, and the communications electronics configured to communicate a detection of the target molecule, and (iii) a fluid conductor configured to conduct the EBC liquid sample to the biosensor, and a microprocessor configured to acquire from an individual patient chemical biomarker data from the biosensor and non-chemical biometric data determined for the individual patient, the communications electronics including a transmitter for transmitting the chemical biomarker data and the non-chemical biometric data as individual patient data;

a remote server for receiving the individual patient data for aggregation with corresponding other patient data received from a set of other patients;

an AI agent running on the remote server configured to analyze the aggregated data to identify patterns and trends and to dynamically control operation of the diagnostic device based on the identified patterns and trends, where the individual patient data is aggregated with the corresponding other patient data received to form a first aggregated data set, where the first aggregated data set is used to train the AI agent to form a model to identify clusters having similar chemical biomarker and/or non-chemical biometric data as the individual patient and to estimate cluster-specific metrics, where the training includes (i) applying an unsupervised algorithm to the first aggregated data set to assign the individual patient to a first order patient cluster that is a subset of the set of other patients, (ii) constructing a labeled training data set from the chemical biomarker and/or non-chemical biometric data of the first order patient cluster, and (iii) applying a trained model algorithm on the labeled training data set to compute first order cluster-specific metrics for the first order patient cluster and produce trained model parameters based on the labeled training data set and generating feedback, based on the trained model parameters, the feedback provided as automatically implementable actions to improve efficacy of the diagnostic system; and a receiver at the first diagnostic device for receiving the feedback from the remote server, wherein the microprocessor automatically reconfigures operation of the first diagnostic device in response to the feedback by modifying at least one physical or electronic operating parameter of the diagnostic device, including adjusting at least one operational parameter selected from the group consisting of a diagnostic threshold, an EBC sampling frequency, a biomarker detection configuration, and an alert routing parameter.

21. The diagnostic system of claim 20, wherein the AI agent is configured to personalize the selection of biomarkers to be detected based on a risk profile of the individual patient.

22. The diagnostic system of claim 20, wherein the AI agent is configured to control the first diagnostic device where the automatic control comprises at least one of:

dynamically adjusting thresholds for diagnostic test results;

modifying an applied therapeutic treatment;

adjusting the frequency of EBC collection and analysis;

updating a probability model for analyzing the aggregated data;

issuing alerts for emerging outbreaks or anomalies detected in population-level data;

issuing alerts to an individual patient or a caregiver;

modifying a software user-interface to suggest changes in time or frequency of use of a testing system;

changing a biosensor to detect a new biomarker;

changing algorithms running on a remote server to include a new AI agent;

creating a design of experiments (DOE) to optimize hardware or software components;

updating payer feedback or reporting systems based on improved patient outcomes or cost savings; and refining testing thresholds based on applied probabilistic analysis.

23. The diagnostic system of claim 20, wherein the AI agent is configured to adjust user feedback to optimize the yield of exhaled breath condensate collection in real time.

24. The diagnostic system of claim 10, wherein the AI agent is configured to issue alerts to the patient based on regional public health data and detected outbreak trends.

25. The diagnostic system of claim 20, wherein the AI agent is trained and updated using clinical outcome data from a population of patients.

26. The diagnostic system of claim 20, wherein the non-chemical biometric data includes physiological signals obtained from wearable sensors.

27. The diagnostic system of claim 10, wherein the AI agent is configured to dynamically adjust the interval between sample collection events based on variation in biomarker levels.

28. The diagnostic system of claim 20, wherein the device is configured to provide diagnostic and trend data to a telemedicine provider dashboard.

29. The diagnostic system of claim 20, wherein the AI agent is configured to adapt the diagnostic operation for pediatric or adult patients.

30. The diagnostic system of claim 20, wherein the AI agent is configured to retrain its biomarker detection model based on newly received population-level data.

31. The diagnostic system of claim 20, further comprising a second diagnostic device for determining the non-chemical biometric data.

32. The diagnostic system of claim 20, where the one or more biosensors comprise at least one lateral flow assay and/or electronic biosensor.

* * * * *